United States Patent
Barbieri et al.

(10) Patent No.: US 9,771,437 B2
(45) Date of Patent: Sep. 26, 2017

(54) POLYELECTROLYTIC POLYMERS, PROCESS FOR THEIR PREPARATION AND USES THEREOF

(71) Applicant: ITALMATCH CHEMICALS S.P.A., Genoa (IT)

(72) Inventors: Antonio Alberto Lucio Barbieri, Qualiano NA (IT); Manuela Crisci, Qualiano NA (IT)

(73) Assignee: ITALMATCH CHEMICALS S.P.A., Genoa (IT)

( * ) Notice: Subject to any disclaimer, the term of this patent is extended or adjusted under 35 U.S.C. 154(b) by 0 days.

(21) Appl. No.: 15/124,438

(22) PCT Filed: Mar. 10, 2015

(86) PCT No.: PCT/IB2015/051733
§ 371 (c)(1),
(2) Date: Sep. 8, 2016

(87) PCT Pub. No.: WO2015/136438
PCT Pub. Date: Sep. 17, 2015

(65) Prior Publication Data
US 2017/0107310 A1    Apr. 20, 2017

(30) Foreign Application Priority Data

Mar. 11, 2014  (IT) .............................. RM2014A0119

(51) Int. Cl.
| | | |
|---|---|---|
| C08F 20/02 | (2006.01) | |
| C02F 1/56 | (2006.01) | |
| A61K 8/81 | (2006.01) | |
| A61Q 19/00 | (2006.01) | |
| C11D 3/37 | (2006.01) | |
| B01D 17/04 | (2006.01) | |

(52) U.S. Cl.
CPC ............ *C08F 20/02* (2013.01); *A61K 8/8147* (2013.01); *A61K 8/8152* (2013.01); *A61Q 19/00* (2013.01); *B01D 17/047* (2013.01); *C02F 1/56* (2013.01); *C11D 3/3757* (2013.01); *C11D 3/3769* (2013.01); *A61K 2800/48* (2013.01); *A61K 2800/5424* (2013.01); *A61K 2800/5426* (2013.01); *A61K 2800/5428* (2013.01)

(58) Field of Classification Search
None
See application file for complete search history.

(56) References Cited

U.S. PATENT DOCUMENTS

| | | |
|---|---|---|
| 3,023,162 A | 2/1962 | Fordyce et al. |
| 4,319,013 A | 3/1982 | Cabestany et al. |
| 4,396,513 A | 8/1983 | Haldeman |
| 4,396,752 A | 8/1983 | Cabestany et al. |
| 4,699,951 A | 10/1987 | Allenson et al. |
| 5,100,561 A | 3/1992 | Wood et al. |
| 2005/0264903 A1 | 12/2005 | Chee |

FOREIGN PATENT DOCUMENTS

| | | |
|---|---|---|
| CN | 1986580 A | 6/2007 |
| CN | 100445305 C | 12/2008 |
| JP | 2003048915 A | 2/2003 |

OTHER PUBLICATIONS

Italian Search Report of IT priority application No. IT RM2014A000119 dated Nov. 4, 2014.
International Search report of PCT/IB2015/051733 dated Jul. 7, 2015.
NTP-CERHR Monograph on the Potential Human Reproductive and Developmental Effects of Acrylamide—Lilianne Abramsson Zetterberg, National Toxicology Program US Department of Health and Human Services, FNIH Publication No. 05-4472, Feb. 2005.
Polyelectrolytes for water and Wastewater Treatment, Sludge Dewatering, William L.K. Schwoyer, Chapter 6.
Polyelectrolytes for water and Wastewater Treatment, The Use of Polyelectrolytes in Filtration Prcesses, L.B. Luttinger, Chapter 7.
DNA damage and DNA adduct formation in rat tissues following oral administration of acrylamide, Isabelle Maniere et al., Elsevier, 2004.
Toxicological effects of acrylamide on rat testicular gene expression profile, Hye-Jin Yanga, Elsevier, Oct. 8, 2004.
Mechanisms of Acrylamide Induced Rodent Carcinogenesis, James E. Klaunig et al., Chemistry and Safety of Acrylamid in Food, edited by Friedman and Mottram, Springer Science+Business Media, Inc., 2005.
The carcinogenicity of acrylamide, Jerry M. Rice, Elsevier, Sep. 26, 2004.

*Primary Examiner* — Samantha Shterengarts

(57) ABSTRACT

The present invention describes the preparation of highly-performing "Acrylamide Free" polyelectrolytic polymers by using not toxic monomers and the way such new monomers can be advantageously used in the field of several civil and/or industrial applications. The new polyelectrolytic polymers developed herein can be then used both as replacement of the common acrylamide-based polymers and in the applications wherein the absence of residual toxic polymerization monomers is requested.

18 Claims, 4 Drawing Sheets

Graph 1

Graph 2

Graph 3

Graph 4

Graph 5

Graph 6

POLYELECTROLYTIC POLYMERS, PROCESS FOR THEIR PREPARATION AND USES THEREOF

RELATED APPLICATIONS

This application is a US national phase application of international application No. PCT/IB2015/051733, filed Mar. 10, 2015, which designates the US and claims priority to Italian Application No. RM2014A000119 filed Mar. 11, 2014, the contents of each of which are hereby incorporated by reference as if set forth in their entireties.

TECHNICAL FIELD OF THE INVENTION

The present invention describes the preparation of highly-performing polyelectrolytic polymers "Acrylamide Free" by using not toxic monomers and how such new monomers can be advantageously used in the field of several civil and/or industrial applications: as flocculating agents for sludge from wastewater chemical-physical and/or biological treatments, coagulating agents in the mixtures for paper mills for the production of paper and/or paperboard, demulsifiers in the petrochemical field, thickening agents in the field of extractive industry, thickening agents used in the detergent and/or cosmetic industry. The new polyelectrolytic polymers developed herein then can be used both as replacement of the common acrylamide-based polymers and in the applications wherein the absence of polymerization residual toxic monomers is requested. An additional advantage of the new polymers is that these can be used and dosed by means of the same apparatuses used for the acrylamide-based polymers.

PRIOR ART STATE

Flocculation consists in a chemical-physical process leading to the formation of a colloidal system wherein the solid phase tends to separate by forming flocs under suspension.

Adsorption phenomena underlie the process, whereas the pH, the temperature and the ionic force are environmental factors which strongly influence flocculation.

A polymer (poly-electrolyte) can create a bridge with the particles and form an aggregate when a particle under suspension is well mixed with the flocculant agent, and the adsorption of the polymer on the surface thereof is energetically favourable.

The poly-electrolytes represent effective flocculants with low concentrations as, thanks to the length thereof (1-30 MD), they are able to join two electric double layers, thus decreasing the particles' need to approach closely the coagulum.

The ionic macromolecules most used on the market of the poly-electrolytes are PAMs, that is the Poly-acrylamides with very high molecular weight wherein the monomer Acrylamide is co-polymerized with cationic or anionic functional monomers; such type of products covers 95% of the world market (evaluated higher than 1,200,000 t/y in 2008). Such products, if from a functional point of view performs well the purpose, from an environmental and healthy point of view are dangerous. The dangerousness of PAMs cannot be identified in the "polymer" but in the acrylamide residue remaining "together with the polymer" after polymerization. Furthermore, the chemical risk is associated to the production of acrylamide, to the storage, transportation, handling thereof.

The use of cationic and/or anionic polymers for treating waters is known in literature ("Polyelectrolytes for Water and Wastewater Treatments" chapters 6, 7—W. L. K. Schwoyer, CRC Press, 1981) and from what determined it is possible to put in relation the molecular weight of a polymer and the charge thereof with its flocculant capability.

Furthermore some authors describe the use of cationic homo-polymers quaternized with ethylene oxide or propylene oxide such as polymers to be used in the dehydration of sludge coming from wastewater treating plants (Fordyce, et al. U.S. Pat. No. 3,023,162). Furthermore, the U.S. Pat. Nos. 4,319,013 and 4,396,752 (Cabestany et al) report how acrylamide- and quaternized Dimethyl-amino-ethyl-acrylate-based cationic co-polymers can be used as agents for the dehydration of sludge.

Other authors such as Haldeman (U.S. Pat. No. 4,396,513) highlight the use, in the dehydration of sludge of cationic polymers mainly constituted by acrylamide and a cationic monomer such as the Dimethyl-amino-ethyl methacrylate quaternized with the Methyl Chloride; such polymers showed having an average molecular weight in the order of one MD.

Moreover, in the U.S. Pat. No. 4,699,951 (Allenson et al.) the discovery and use in the dehydration of sludge of two different cationic polymers with different molecular weight were claimed.

In the U.S. Pat. No. 5,100,561 (Wood et al.) the authors of the study highlight how some types of homo-cationic polymers, with suitable molecular weight, can be applied in the dehydration of process sludge. The average molecular weights of the homo-polymers described by them, on the average low due to the synthesis process applied thereby, did not guarantee great performance.

In the current state of art almost all polymers, poly-electrolytes, used on the worlds market as flocculating agents on sludge, as retentive agents of mixture in paper mill, as agents of clari-flocculation in the purification of the drinking water and/or used as thickening agents, are acrylamide-based.

Acrylamide is a toxic substance, classified carcinogenic of category 1B, is an accumulation neurotoxic substance, then there are all problems inherent the industrial handling thereof with the risks directly connected to the exposition of the professional personnel.

In the last 15 years innumerable studies have followed one another which have investigated the toxic effects of Acrylamide both on man, and on animals and on the environment. To this regard, the following most recent bibliographic references are mentioned:

Klaunig J E, Kamendulis L M. Mechanisms of acrylamide induced rodent carcinogenesis. Adv Exp Med Biol 2005; 561:49-62.

Maniere I, Godard T, Doerge D R, Churchwell M I, Guffroy M, Laurentie M, et al. DNA damage and DNA adduct formation in rat tissues following oral administration of acrylamide. Mutat Res 2005; 580(1-2):119-29.

National Toxicology Program, Center for the Evaluation of Risks to Human Reproduction (NTP-CERHR). Monograph on the Potential Human Reproductive and Developmental Effects of Acrylamide. February, 2005. NIH Publication No. 05-4472.

Rice J M. The carcinogenicity of acrylamide. Mutat Res 2005 Feb. 7; 580(1-2):3-20.

Yang H J, Lee S H, Jin Y, Choi J H, Han D U, Chae C, Lee M H, Han C H. Toxicological effects of acrylamide on rat testicular gene expression profile. Reprod Toxicol 2005; 19(4):527-34.

ECHA, within the application of REACH Regulation, on 30 Mar. 2010, with Decision ED/68/2009, has included acrylamide in the list of the Substances of Very High Concern (SVHC).

The purpose of REACH Regulation is to identify the substance which would have serious effects on the human health or on the environment, to check adequately the risks linked to the use of such substances (which, if possible, have to be gradually replaced) and to provide the authorization thereof only for specific and controlled uses.

Having stated this in advance, the possibility of having available poly-electrolytes manufactured without the use of acrylamide monomer would allow to remove from the market this dangerous substance, thus avoiding the production, handling and transportation thereof.

Unfortunately, the search performed by the present applicant has demonstrated that the simple replacement, in the classic polymerization process, of the acrylamidic monomer with less toxic, acrylic or not acrylic, monomers, even if strongly correlated to acrylamide, produces polymers the performances thereof are unsatisfactory with respect to the acrylamidic polymers and insufficient for an industrial application.

The object of the present invention is then to produce new polyelectrolytic polymers without using acrylamidic monomer, that is "acrylamide-free" polymers, which however offer performances at least comparable to those offered by the acrylamidic polymers.

SUMMARY OF THE INVENTION

The present invention is based upon the finding that, by modifying the polymerization method of acrylic monomers different from acrylamide, new "Acrylamide Free" polyelectrolytic polymers can be obtained having application parameters perfectly comparable to those of the products with acrylamidic base in commerce and in some cases even better.

In particular, the new polymers of the invention can be produced and used in the applications mentioned before without any pollution and/or restrictive constraint, thus by falling in the category of the "green chemicals". Furthermore, said polymers, produced in water-in-oil emulsion, can be advantageously used with the same dilution and dosage systems currently used for the acrylamide-based standard products.

Therefore, a first subject of the invention is a process for preparing an acrylamide-free acrylic polymer comprising the following steps:
a) preparing a reaction mixture containing the monomer or the mixture of monomers and suitable polymerization additives,
b) adding the polymerization catalyst in a controlled manner,
c) allowing the polymerization reaction to proceed until the polymer is obtained,
characterized in that the monomer or the mixture of monomers is not or does not comprise acrylamide, the reaction mixture is a water in oil emulsion and the polymerization reaction is carried out at a controlled temperature between 30° C. and 45° C., that is between 35° C. and 40° C., that is between 35° C. and 38° C.

In an embodiment of the invention, said process is characterized in that the reaction temperature is kept under the defined threshold by adding the catalyst in a controlled manner and by heating or cooling the mixtures according to needs.

In another embodiment of the invention the catalyst addition takes place by continuous supplying or by pulsed dosing throughout the reaction time.

In another embodiment the water in oil emulsion is obtained by mixing an oil phase containing a surfactant having low HLB value and an aqueous phase containing the monomer or the mixture of monomers, the catalysis promoters and usual polymerization additives.

In another embodiment the mixture of monomers comprises crosslinking monomers.

In another embodiment the process comprises an additional step of the polymerization completion (burn-out).

In an additional embodiment the process can comprise an additional step wherein an inversion surfactant of the emulsion having high HLB value is added to the reaction emulsion.

A second subject of the invention is an acrylic polymer obtainable with the invention process, not containing acrylamide monomer units, as acrylamide is not used in the process for preparing the polymer. In particular a polymer equipped with one or more of the following properties:
Molecular weight of the polymer comprised between 5 MD and 30 MD;
Bulk viscosity of the polymeric emulsion comprised between 500 cPs and 2500 cPs;
polymeric UL viscosity comprised between 3 cPs and 60 cPs (in standard solution);
Percentage of Solid in the emulsion comprised between 35% and 50%;
Viscosity in aqueous Solution with 0.5% of active at 25° C. comprised between 150 cPs and 8000 cPs;
Dissolution in water time expressed in seconds comprised between 1 s and 15 s.

A third subject of the invention is a polymeric composition in the form of water in oil emulsion comprising the acrylic polymers of the invention and an inversion surfactant, capable of reversing the water in oil emulsion into an oil in water emulsion, after mixing the polymeric composition itself to the aqueous medium to be used in final applications.

Additional subjects of the invention are the uses of the composition of the invention as flocculating agent, retentive agent, coagulating agent, demulsifier, thickening agent.

Other additional subjects of the invention are:
Methods for cleaning wastewaters or sludge from chemical, physical and/or biological waste water treatments, comprising a step wherein the acrylic polymers or compositions containing them according to the invention are mixed under stirring with said waste waters or sludge. Methods for coagulating or retaining the mixtures for paper mills for the production of paper and/or paperboard, comprising a step wherein the acrylic polymers or compositions containing them according to the invention are mixed under stirring with said mixtures for paper mills.

Methods for demulsifying or thickening processing products of the petrochemical or extraction industry, comprising a step wherein the acrylic polymers or compositions containing them according to the invention are mixed under stirring with said processing product mixtures for paper mills.

Methods for thickening products of the detergent or cosmetic industry, comprising a step wherein the acrylic polymers or compositions containing them according to the invention are mixed under stirring with said products.

DETAILED DESCRIPTION OF THE INVENTION

Figure 1:
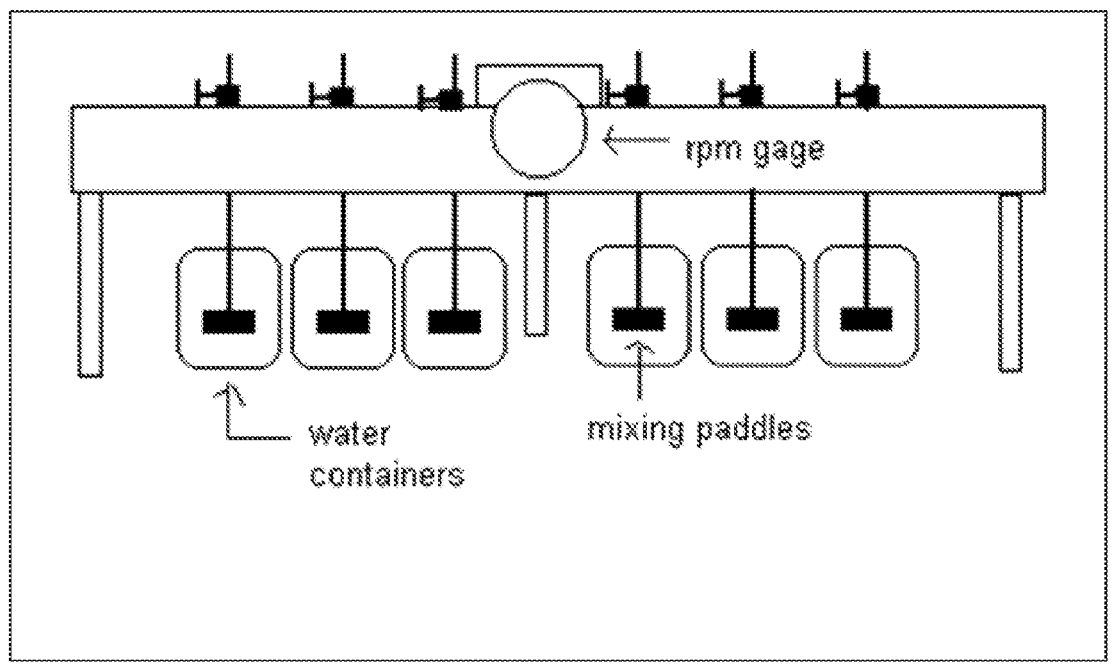
FIG. 1: the figure illustrates a typical apparatus for carrying out the Jar Test.

The polymers subject of the invention can be homo-cationic, homo-anionic, zwitterionic or a different set based upon different monomers. In particular they can be cationic homo-polymers, cationic co-polymers, cationic ter-polymers; anionic homo-polymers, anionic co-polymers, anionic ter-polymers; zwitterionic co-polymers, zwitterionic ter-polymers.

Such poly-electrolytes manufactured with the synthetic methods described in the present application have molecular weights suitable to a cheap end effective flocculation process.

Methods for Preparing Polymers of the Invention
The Monomers

The present inventors have performed a series of pre-screening tests aimed at detecting cationic and anionic acrylic and not acrylic monomers able to provide polymers with high molecular weight. The percentage values of Standard Chemical Reactivity (RCS %) of the single monomers with respect to the chemical reactivity of acrylamide have been calculated. Such value is a measurement of the capability of a monomer to form homo-polymers under standardized operating conditions. The operating parameters of the method for calculating RCS % are shown in the experimental section of the present patent application; the method for calculating the RCS % has been wholly developed by GRS. The method for determining the RCS % value assumes as method basis a reaction temperature comparable to that usually used for the industrial synthesis of acrylamide-based polymers, even if in the latter case the polymerization can be performed at a slightly lower temperature (50-55° C.).

Some monomers analysed, by way of example, by the present inventors and the RCS % "standard" values thereof are shown in table 1 (together with the corresponding CAS figures).

TABLE 1

| n. | Monomer name | CAS | RCS % |
|---|---|---|---|
| 1 | Acryloxyethyltrimethyl Ammonium chloride (AETAC) | 44992-01-0 | 23.35 |
| 2 | Methacryloxyethyltrimethyl Ammonium Chloride (METAC) | 5039-78-1 | 19.68 |
| 3 | Dimethylaminoethyl Methacrylate DMS Quaternary | 6891-44-7 | 18.52 |
| 4 | Dimethylaminoethyl Acrylate DMS Quaternary | 13106-44-0 | 21.7 |
| 5 | Dimethyldiallyl Ammonim Chloride (DADMAC) | 7398-69-8 | 17.88 |

TABLE 1-continued

| n. | Monomer name | CAS | RCS % |
|---|---|---|---|
| 6 | Acrylic Acid | 79-10-7 | 83.38 |
| 7 | Methacrylic Acid | 79-41-4 | 61.36 |
| 8 | 2-Acrylamido-2-Methylpropanesulfonic Acid | 15214-89-8 | 65.37 |
| 9 | Sodium Styrenesulfonate | 2695-37-6 | 58.15 |

By assigning conventionally the RCS 100% value to the acrylamide monomer, values lower than 100% will show a lower capability of the monomer to form homo-polymers, whereas values higher than 100% will show monomers with a polymerization capability higher than that of acrylamide.

Then, the RCS % value is a parameter which indirectly reflects the performance of the obtained polymer. In fact, a high RCS % value reflects in a high viscosity of the polymeric solution obtained against a high molecular weight of the synthetized polymer, which then will have good performances in the industrial applications. Viceversa a low RCS % value reflects in a low viscosity of the polymeric solution, then low molecular weight of the synthetized polymer, and then poor performances of the polymer in the industrial applications.

From Table 1 it can be seen that any monomer, among the studied ones, has strongly lower RCS % value than 100% (the reference value associated to a poly-acrylamide), and then it will produce, the synthesis (above all temperature) operating conditions being equal, homo-polymers with lower molecular weight than those obtained by acrylamide and then homo-polymers with unsatisfactory application performances.

However, the present inventors have found that the RCS % values of the same monomers can be strongly improved by modifying the profile of the polymerization temperature of the RCS % method as described hereinafter, by operating under gentler and more controlled conditions with respect to the usual method.

In fact, upon reducing the polymerization temperature in the RCS % method (i.e. 60° C.) or in the industrial process for preparing acrylamide polymers, (i.e. 50-55° C.) at a temperature comprised between 30° C. and 45° C., better between 35° C. and 40° C., and still better between 35° C. and 38° C., preferably around 37° C., for example 35.5° C., 36° C., 36.5° C., 37° C., 37.5° C., one succeeded in increasing, at least partially, the low RCS % of the monomers of Table 1.

The RCS % values corresponding to the monomers mentioned in Table 1 and obtained by acting under the above-described conditions are shown by way of example in Table 2 below.

TABLE 2

The modified RCS % of the monomers at 37° C. versus Poly-Acrylamide at 60° C.

| n. | Monomer Name | CAS | RCS % |
|---|---|---|---|
| 1 | Acryloxyethyltrimethyl Ammonium chloride (AETAC) | 44992-01-0 | 40.00 |
| 2 | Methacryloxyethyltrimethyl Ammonium Chloride (METAC) | 5039-78-1 | 32.47 |
| 3 | Dimethylaminoethyl Methacrylate DMS Quaternary | 6891-44-7 | 29.15 |
| 4 | Dimethylaminoethyl Acrylate DMS Quaternary | 13106-44-0 | 35.55 |
| 5 | Dimethyldiallyl Ammonium Chloride (DADMAC) | 7398-69-8 | 32.14 |
| 6 | Acrylic Acid | 79-10-7 | 122.94 |

TABLE 2-continued

The modified RCS % of the monomers at
37° C. versus Poly-Acrylamide at 60° C.

| n. | Monomer Name | CAS | RCS % |
|---|---|---|---|
| 7 | Methacrylic Acid | 79-41-4 | 105.36 |
| 8 | 2-Acrylamid-2-Methylpropanesulfonic Acid | 15214-89-8 | 92.06 |
| 9 | Sodium Styrenesulfonate | 2695-37-6 | 89.68 |

Therefore acrylic monomers suitable to the present invention, used singularly or in mixture, are those having a RCS % value, under polymerization conditions according to the present invention, of at least 30%, for example 30%, 35%, 40%, 50%, but preferably higher than 50%, for example 60%, 70% 80%, 90% or 95% or even better equal or higher than 100%, for example 105%, 110%, 120%, 130%, 150%, 170%, by excluding acrylamide. Apart from the above mentioned monomers any vinylic or allylic monomer with hydrosoluble polar groups can be used for the purpose.

Other cationic monomers which can be used for the purpose are: dimethylaminoethyl acrylate benzyl chloride quaternary salt, dimethylaminoethyl acrylate sulphuric acid salt, dimethylaminoethyl acrylate hydrochloric acid salt, diethylaminoethyl acrylate methyl chloride quaternary salt, diethylaminoethyl methacrylate, diethylaminoethyl methacrylate methyl chloride quaternary salt, methacrylamidopropyl-trimethylammonium chloride, acrylamidopropyltrimethylammonium chloride, dimethylaminopropylacrylamide methyl sulphate quaternary salt, dimethyl-aminopropylacrylamide sulphuric acid salt, dimethylaminopropylacrylamide hydrochloric acid salt, diallyldiethylammonium chloride, diallyldimethyl ammonium chloride, diallylamine, vinylpyridine.

Other anionic monomers which can be used for the purpose are:
vinyl sulphonic acid, salts of vinyl sulfonic acid, vinylbenzene sulphonic acid, salts of vinylbenzene sulphonic acid, alpha-acrylamidomethylpropanesulphonic acid, salts of alpha-acrylamidomethylpropanesulphonic acid, 2-sulphoethyl methacrylate, salts of 2-sulphoethyl methacrylate, salts of acrylamido-2-methylpropanesulphonic acid, maleic acid, fumaric acid, itaconic acid, succinic acid, styrenesulphonate and its salts. Moreover, all selected monomers are hydrosoluble as, once finished they poly-electrolytes, they will have to explicit the functionality thereof in the aqueous medium.

Method for Preparing the Acrylamide-Free Polymers of the Invention

The herein described "Acrylamide Free" polyelectrolytes are obtained by means of a synthesis process in "water-in-oil" emulsion under delicate and suitably controlled conditions.

The method comprises the following passages:
i) preparation of the oil phase;
ii) preparation of the aqueous phase;
iii) preparation of the emulsion;
iv) polymerization reaction;
v) removal of traces of free residual monomer;
vi) emulsion inversion.

The passages (v) for removing the monomer traces and (vi) for inverting the emulsion, even if preferably existing, are optional. The passage (iv) is that having greatest importance.

i) The Preparation of Oil Phase:
The oil phase is prepared inside a mixer with volume suitable to the quantity of polymer to be produced, for example a 3-liter mixer. The components of the oil phase usually are: an oily solvent, for example a paraffinic high-boiling one (such as for example Exxsol D 100 of Exxon-Mobil Chemicals) strongly without sulphur and without flavour and one or more surfactants with low HLB, in the range 3.0-6.0 such as, for example: glycerin mono-stearate, ethylenic-monostearate glycol, glycerin fat esters, mono-stearate poly-ethylene-glycols, tallow-amine-etoxylate, nonil-phenol-etoxylate, etoxylate fat alcohols with 2 moles of ethylene oxide, sorbitan-monooleate, sorbitan-dioleate, sorbitan-trioleate, sorbitan-monostearate, oleil-isopropanolamine. Some of these surfactants are commercialized with tradenames such as: Sorbitol or—sorbitan-monooleate—by Lamberti S.p.A and Burcomide 61—Oleic acid Isopropanolamide—by Burco Chemicals), apt to create a stable "water-in-oil" emulsion. Once weighed, the single components are introduced into the mixer and left to be stirred until obtaining an homogeneous phase at the temperature of about 25° C. At this point the oil phase is ready to be used.

ii) The Preparation of the Aqueous Phase:
The aqueous phase is prepared inside another mixer with suitable volume, for example a 2-liter mixer. Even in this case the typical components of the aqueous phase are: the hydrosoluble monomers (with specific reference to those designated in table 1), demineralized water (or by osmosis), catalysis promoters, transferring agents (for obtaining the molecular weight in a suitable way), anticoagulants (which will prevent the iper-polymerization of monomers with formation of gels), cross-linking agents as defined below, oxido-reducting catalysis promoters, excipients, complexing agents. Once the various components have been weighed, they are inserted inside the mixer and they are let under stirring until the solution is homogeneous at a temperature of about 25° C.

Once the aqueous phase is homogeneous, the pH is measured (with a pH-meter calibrated in the range 7.0-4.0). The solution pH is brought to 5.0±0.2 for the cationic emulsions and 7.5±0.2 for the anionic and zwitterionic ones. The pH of the solutions is obtained by adding, slowly with suitable measuring device, for example a Pasteur pipette, a solution of 30% (w/w) sulphuric acid or 32% (w/w) ammonia.

Once reached the wished pH value the aqueous phase is ready to be used.

iii) The Preparation of the Emulsion:
When both reaction phases are ready, one proceeds with the preparation of the reaction mixture under form of emulsion. On the average the oil phase/water phase ratio is 25/75 w/w.

To this purpose the aqueous phase is poured into the oil phase and everything is homogenized by using a high efficiency and speed immersion mixer. The homogenization time depends upon the size of the wished emulsion micellae; high homogenization time will lead to highly homogeneous (strict gaussian) and stable small micellae (0.5-1.5 microns). Once prepared the emulsion the bulk viscosity (Bulk Raw) thereof is measured with a digital viscometer. Such parameter is index of homogenization process efficiency. On the average the optimum viscosity range of a polymerizable raw emulsion is 1000-1500 cPs @ 25° C.

iv) The Polymerization Reaction:
The Polymerization Reactor
The reaction is performed in a reactor, which can be sealed, with suitable volume equipped with the following instruments: preferably mechanical stirring means, heating and cooling means, manual or automatic, even programmable, means for measuring and controlling the temperature in the various reaction phases, inlet/outlet for the gases and means for controlling the flow, means for adding reagents.

In particular, the reactor must be equipped with means for adding or supplementing the catalyst or the mixture of catalysts used in the reaction. Such means are suitable for on time dosages, also called "shot" or pulsed dosages, at fixed and predetermined moments of the reaction. Alternatively such means are suitable for feeding the catalyst with a continuous flow in a predefined period of time. In each case the means for feeding or dosing the catalyst have to guarantee a controlled supply in terms of dosed quantity, feeding time. Such means for dosing the catalyst or the catalysts can be, for example, syringe pumps or peristaltic or microperistaltic, even automatic, dosing devices. It is not essential for the invention that the reactor has available all above-enlisted functions, if some of them can be provided by outer instruments. At last, the reactor can be equipped with an automatic, even programmable, control system linking the quantity of dosed catalyst and/or the dosing time (length or timing) to one or more parameters of the polymerization mixture, for example viscosity, but preferably the reaction temperature, so as to keep such parameter below a predefined threshold, thus allowing the need minimum use of the catalyst.

The Procedure

The emulsion is placed in the reactor in inert atmosphere, for example in nitrogen atmosphere. After stabilization in inert environment, to the rough emulsion the requested quantity of catalysis promoter is added (see the subsequently described synthesis method "A" requesting the activation of a complex catalysis mechanism based upon an oxide-reductive mechanism) (to be selected in the class of the radical initiator such as Luperox® TBH70X—t-butyl hydroperoxide—or Luperox® DI—tert-Butyl peroxide by Arkema, upon dilution thereof in demineralized water).

The mixture is brought and kept in inert atmosphere for about 60 minutes at the temperature of 25° C. Therefore, the polymerization catalyst is added in a controlled manner, which starts the polymerization reaction, by leaving the reaction to proceed. Considering that the polymerization reaction is an exothermal reaction, the catalyst dosing has to be so as to bring the reaction temperature, on time, to the above-described values, that is at a temperature comprised between 30° C. and 45° C., better between 35° C. and 40° C., and even better between 35° C. and 38° C., preferably around 37° C., for example 35.5° C., 36° C., 36.5° C., 37° C., 37.5° C., without exceeding such threshold value. Said mode for adding the catalyst thus allows the precise control of the reaction development and, advantageously, the use of the needed minimum quantity of the catalyst itself by allowing to obtain a higher molecular weight of the polymer.

The catalyst feeding or dosing can take place according two modes, during the whole reaction time:
1. By using a programmable syringe pump wherein the polymerization catalyst in aqueous solution is fed with continuous but variable flow. In fact the catalyst flow is adjusted so that the emulsion reaches the reaction stationary temperature in the wished time (time Ramp). For example, the temperature increase due to the catalyst has to be so as to bring the reacting emulsion from the temperature of 25° C. to that of 37.5° C. in a period of time equal to 60 minutes ($\Delta t=0.2083°$ C./min). Such temperature depends upon the polymer type which one wants to obtain. Low polymerization temperatures 32-38° C. will favour high molecular weights.

2. With pulsed ("shot") dosage, with suitable fixed reaction time, in case of catalysts with low release of radicals.

When the emulsion reaches the requested synthesis stationary temperature the insulating blanket is removed (the reactor can exchange thermically with the surrounding environment—gentle cooling) and the polymerization is kept, by adjusting the catalyst flow and/or the reactor cooling by means of ice bath. When the emulsion temperature cannot be kept anymore and it decreases, the quantity of fed catalyst is increased.

The reaction will proceed in this way until exhausting its own reactivity (polymerization of all double bonds).

v) The Burn-Out (or Polymerization Completion Phase)

Once completed the reaction catalyst dosing or feeding, the burn-out catalyst is added to the emulsion. The burn-out phase is that of the polymerization reaction wherein a strong excess (from 20% to 200%, preferably from 20 to 100%) of radical catalyst to force the last traces of monomer not reacted to polymerize and avoid the presence thereof in the finished polymer. The burn-out catalyst can be similar, or different, to the one used during the polymerization reaction. From studies performed on the free residual monomer determination after the polymerization phase, GRS has selected an overdosage of a radical catalyst based upon a cuprous/cupric ion oxide-reductive mechanism.

vi) Emulsion Inversion: The Inversion Surfactants:

With the help of suitable means, for example a syringe, the suitable quantity of inversion surfactants is added cautionally to the reaction emulsion. Such surfactants have the purpose of "inverting" the "water-in-oil" polymeric emulsion, when this is additioned to the aqueous means or to the water for preparing the poly-electrolyte solution to be used in the provided final applications. In fact the inversion surfactants have the task of emulsioning in the preparation water the hydrocarbon phase of the polymeric emulsion, thus by releasing the aqueous poly-electrolyte micellae contained therein by allowing at last the dissolution thereof in water. At the end of the dissolution process there will be then an "oil-in-water" emulsion. Surfactants, or mixtures of surfactants, apt to this purpose are those with a HLB in the range 8-18. Some examples of usable specific surfactants are: ethoxylated alcohols with fat chain $C_8$-$C_{20}$, propoxylated alcohols with fat chain $C_8$-$C_{20}$, ethoxylated/propoxylated copolymers, dialkyl-sulfosuccinates with fat chain, ethoxylated fat acids, propoxylated fat acids, poly-glycol-etoxylates, triglyceride-ethoxylates, triglyceride-propoxylates, nonylphenol ethoxylates, nonylphenol propoxylates. Some of these surfactants are commercialized with the following tradenames: Empilan KB7, commercialized by Huntsman, which results to be an ethoxylated Alcohol $C_{12}$-$C_{14}$ with 7 molecules of Ethylene Oxide, Tergitol 15-S-7, commercialized by Dow Chemicals, which results to be an ethoxylated secondary alcohol with 7 molecules of ethylene oxide. Once completed the addition of the surfactant, the obtained polymer is left to be stirred for a suitable period of time, for example about 60 minutes. An optimum solubilization of the inversion surfactant in the emulsion is the condition for a good operation of the product. A main feature of the inversion method is represented by the catalysis system in the polymerization reaction. Two distinct methods, "A" and "B", were processes, apt to determine the maximum molecular weight of the end polymer within the synthesis.

The "A" Method is based upon a radical oxide-reductive system which can be controlled by means of suitable dosing of the reducing component; this allows controlling the development of the polymerization kinetics and, partially, the reaction temperature. The mechanism scheme is shown herebelow. The catalysis process can be triggered in a temperature range from 20 to 30° C. and controlled by means of reducing dosage.

$$R^1O-OH+CHE-Cu^+ \rightarrow R^1O^*+OH^-+CHE-Cu^{++}$$

[Initiation reaction]

$$R^1O^*+CH_2=CHR \rightarrow R^1O-CH_2-CHR^*+Monomers \rightarrow Polymer$$

[Propagation reaction]

$$R^1O-(CH_2-CHR)n^*+^*OR^1-(CH_2-CHR)n-OR^1$$

$$R^1O-(CH_2-CHR)n^*+R^1O-(CH_2-CHR)m^* \rightarrow R^1O-(CH_2-CHR)n_+m-OR^1$$

[Termination reactions];

$$2CHE-Cu^{++}+RID+H_2O \rightarrow 2CHE-Cu^++OXI+2H^+$$

[Catalyst regeneration]

In the above-illustrated scheme:
$R^1O-OH$ identifies an organic hydroperoxide wherein $R^1$=t-Butile,
$CH_2=CHR$ identifies a general replaced vinilic monomer wherein $R=-COOH, -COOR^2$,
CHE designates a chelating agent such as: EDTA, DTPA,
RID designates a reducing agent such as: Sodium metabisulphite,
OXI designates the oxidized form of the reducing agent The "B" Method is a radical method with thermal release using the mechanism of homolytic splitting of the Azocompound Wako V 50 (by Wako Chemicals) which acts as catalyst. Other Azocompounds with comparable operation, such as Wako VA 44, can be used for the purpose. In this case the performance of the polymerization reaction is assigned both to the catalyst concentration and, directly, to the reaction temperature which determines the catalyst thermal splitting. The scheme of the catalyst homolytic splitting is shown herebelow:

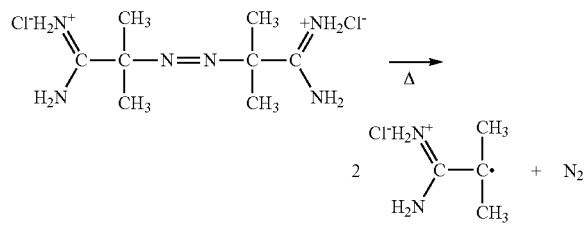

By operating with right catalyst concentration, on the average 100 ppm, and by controlling in a suitable way the temperature of the polymerization reaction (range 35°-37° C.) it is then possible to have a new process with high performance in molecular weight.

As highlighted in the examples, the two catalytic systems "A" and "B" can be used alternatively in the invention method.

Cross-Linked Polymers

Apart from the method variations already described above, it is also possible to modify the structure of the obtained polymers, from linear to cross-linked ones, by using difunctional monomers or mixtures of mono- and difunctional co-monomers.

The cross-linked polymers can differentiated for a higher or lower crosslinking level. Such difference will have a great impact in the polymer performances. On the contrary, highly cross-linked polymers (grid with strict meshes), will lead to the formation of big and mechanically stable "flocs" of sludge by allowing the use of draining centrifuges, downwards the flocculation process, without the risk of "floc" breaking and loose of solid material.

The molecular weight of cross-linked polymers and the suitable grid sizing can be performed by using chain transferring agents according to the below scheme:

$$P\bullet + XR' \longrightarrow PX + R'\bullet$$

wherein: P●=growing polymeric chain
XR'=chain transfer agent
PX=ended polymeric chain
R'●=free radical for a new polymeric chain Suitable chain transfer agents which can be used in the processes described in this work are: Isopropyl Alcohol, 2-Mercapto-ethanol, Isobutylic Alcohol.

As far as the cross-linking or reticulating, bivalent or trivalent, monomers are concerned, these are well known to the person skilled in the art. In the present work, by way of example, two types of bivalent hydrosoluble monomers were used: Methylene bis-acrylamide and Ethylene bis-acrylamide. The structures thereof are shown herebelow.

$$H_2NCOCH=CH-CH_2-CH=CHCONH_2 \text{ (Methylene bisacrylamide)};$$

$$H_2NCOCH=CH-CH_2-CH_2-CH=CHCONH_2 \text{ (Ethylene bisacrylamide)}.$$

It is possible stating the cross-linking degree of a polymer by making reference to the ppms of crosslinking monomer used in the synthesis. In the present work a concentration variable in the range between the minimum value of 3 and the maximum value of 6 ppm was used, but concentrations outside this range can equally be used and they remain within the scope of the present invention. Therefore, since a codified system is not described in literature, a CL (cross-linking) value equal to 0% has been arbitrarily associated for the linear molecules, equal to 50% for the polymers with 3 ppm of cross-linking agent and equal to 100% in case of 6 ppm of cross-linking agent.

The Invention Polymers

The acrylamide-free polymers obtained according to the invention are characterized both by the preparation method thereof and by a series of typical parameters deriving directly from the operating conditions of the method itself.

Appearance or aspect of the emulsion obtained after polymerization: Opaque-translucent viscous liquid;

Molecular weight: comprised between 3 MD and 30 MD;

Bulk viscosity: value in cPs at 25° C. of the viscosity of the polymeric emulsion after polymerization comprised between 500 cPs and 2500 cPs;

UL viscosity: value, in cPs at 25° C., of the standard viscosity measured on the polymer, comprised between 3 cPs and 60 cPs;

Solids %: it is the % (w/w) value of solids present in the emulsion polymer calculated by means of thermo-gravimetric balance at the temperature of 160° C., comprised between 35% and 50%;

Viscosity in 0.5% solution: It is the viscosity of the polymer, expressed in cPs at 25° C., in 0.5% aqueous solution dry base polymeric emulsion, comprised between 150 cPs and 8000 cPs;

Dissolution test: value measured in seconds, and comprised between 1 s and 15 s, necessary to the polymeric emulsion for the dissolution thereof in water under proper standard conditions.

Free monomers: value expressed in mg/Kg of emulsion (or ppm) of the residual concentration of the post-polymerization free monomers. Such value has to be lower than 250 ppm;

Gels %: This value, in % (w/w), expresses the quantity of coagula which have formed during polymerization; such value designates the effectiveness of the synthesis method. Good polymerizations have a value of gels lower than 0.5%.

It is important to remind that the main parameters for the polymer characterization, based thereupon the effectiveness of the polymer in the below-described applications is evaluated, are "UL viscosity" which, among other things, is the direct measurement of the polymer molecular weight, and the Viscosity in 0.5% solution. Low values of these parameters designate industrial poor or insufficient performances.

INDUSTRIAL APPLICATIONS

The acrylamide free polyelectrolytic polymers of the invention can be used in various application fields such as the cleaning of waste water or sludge, paper mills, the petrolchemical and extractive industry, the detergent and cosmetic industry. In particular the polyelectrolyte polymers of the invention can be used as flocculating agents for waste water or for sludge from wastewater chemical-physical and/or biological treatments, coagulants or retentive agents in the mixtures for paper mills for the production of paper and/or paperboard, demulsifiers in the petrochemical field, thickening agents in the field of extractive industry, thickening agents used in the detergent and/or cosmetic industry.

Experimental Portion and Analytical Methods

The polymers obtained according to the invention are evaluated based upon the features and performances thereof. Hereinafter the technical protocols and the methods used for the characterization and performance tests are shown, performed on the present "acrylamide free" polymers.

Determination of the Standard Chemical Reactivity (RCS %) of the Monomers

The object of the present method is to determine the maximum polymeric molecular weight obtainable for a given ionic monomer when this is made to react under determined conditions. The viscosity of the obtained polymeric solution will be a measurement of this capability. With the purpose of assuming a "reference standard", the "100%" value is associated to a poly-acrylamide, synthetized according to this method. Such "100%" is associated to the "average" viscosity measured in 10 standard polymerizations of Acrylamide.

The Operating Procedure is described hereinafter:

The monomer which has to be analysed must be polymerized in a suitably equipped 3-liter reactor.

The standard conditions to be used are:

The polymeric solution to be synthetized must have a reactor mass equal to 2000+/−5 g.

The monomer concentration in the aqueous solution must be equal to 0.03018% in moles (active only).

The solution pH must be 7.00+/−0.5 (by means of 10% Sodium Hydroxide or 30% Sulphuric Acid).

The reaction temperature must be equal to 60° C. (+/−2° C.);

The catalyst must be injected at a temperature of 55° C. (+/−1° C.).

The temperature gradient from 55° C. of the catalyst injection at 60° C. of reaction must be equal to 1° C./min.

The reaction time must be 3 hours before the "burn-out" (+/−5 minutes).

The catalyst concentration, in 1%-active solution, must be equal to 0.25% of the charge to the reactor.

The catalyst must be Wako V 50 (2,2'-Azobis(2-methylpropionamidine)-dihydrochloride)—by Wako Chemicals—which is suitably kept in fridge. Under these conditions the catalyst has a duration equal to 2 years.

The Nitrogen flow, the "sparge", during the whole reaction (with start when loading the monomer(s) and stop after the "burn-out" phase) must be 2 l/min.

The stirring speed of the reactor must be equal to 250 rpm.

A so-synthetized polymer will be "polymerized under RCS conditions".

Determination of the Viscosity of the Polymer and Assignment of the RSC % Value Thereof.

Once obtained the polymer under RCS conditions, the viscosity thereof has to be determined; for such purpose the following viscometer has to be used: DV-I+digital Brookfield equipped with s 63. Depending upon the viscosity of the product under analysis the shaft rotation will be defined. The polymer, before being subjected to the viscosity measurement, has to be thermostated at 25° C. in a 600-ml becker with wide mouth. The polymer must not have inside thereof bubbles and/or concentration, and then viscosity, gradients. The viscosity measurement must be performed 5 times and for calculating RCS the arithmetic mean of the obtained values has to be used.

The RCS calculation is performed in the following way:

$$RCS=Vmm/Vamd*100$$

Wherein: Vmm=average viscosity measured for the unknown polymer.

Vamd=15000 cPs (viscosity std Acrylamide).

100=dimensional factor.

Dissolution Test: In a calibrated 1000-ml becker da 1000 ml, and with high shape, 400 ml of water are put from osmosis. The becker is then placed under mechanical stirrer equipped with suitable stirring rod. By means of the rod a vorticous motion is given to the 400 ml of water therefore the water reaches a vortex height equal to 600 ml. Suddenly, by means of a syringe, a quantity of polymeric emulsion is injected in the "rotating" water so that a polymeric aqueous solution equal to 0.5% in w/w is obtained. Then, one measures the time, in seconds, which the vortex will take to to reach the height of 400 ml in the becker due to the increase in viscosity of the aqueous solution.

The measured time depends upon the structural parameters of the polymeric emulsion and the balancing thereof. Briefly, the vortex lowering expresses an optimum dosing of the release surfactant of the polymer in water and, indirectly, it expresses the molecular weight of the polymer (high molecular weights will request few seconds for lowering the vortex).

Free monomer (free residual monomer): Measurement, by means of HPLC with UV-Vis detector, of the quantity of the free residual monomer after polymerization. From the polymeric emulsion, by means of suitable solvents, the free residual monomers are extracted. The extraction solution, with such monomers, will be then subjected to analytic screening. The best analysis method assumes the use of HPLC techniques with UV-VIS detector. The determination provides the use of a HPLC column such as Spherosorb ODS-1, 5μ, 250 cm×4.6 mm. The determination results will be then compared with the calibration curves developed previously in the methods.

Gels %: 100 g of polymeric emulsion are suitably diluted with 75 g of a high-boiling paraffin solvent such as Exxsol D 100. After suitable homogenization, the so-obtained solution is filtered on suitable 100 micro-meter mesh which has been suitably weighed. After the filtration of the polymeric solution the mesh is washed with the solvent, dried and then weighed again. The gel percentage quantity will be given by the formula:

$$Gel\ \% = [(Pf-Pi)/Pe]*100$$

Wherein: Pf=final weight filtration grid
Pi=initial weight filtration grid
Pe=weight of the analysed emulsion UL Viscosity (UL viscosity): Such viscosity is a parameter directly connected to the molecular weight of a polymer dissolved in water. Polymers with high UL viscosity (>5.00 cPs @ 25° C.) guarantee good performances in the field of flocculation and coagulation. Such viscosity is then an indispensable homologation parameter of a flocculating polymer. The determination of this viscosity is performed by means of Brookfield viscometer equipped with a suitable adapter called "UL adapter". The polymer to be analysed is dissolved in a "standard" saline solution constituted by an inert electrolyte, Sodium Chloride, in the extent of 4.0% in w/w and by a not ionic surfactant with HLB in the range 10-12 in the extent of 0.1%. The polymer under examination is dissolved in the "standard" solution in the extent of 0.3% on the polymeric dry basis. After suitable solubilisation of the polymer by means of mechanical stirring (20 minutes) the value of the UL viscosity is read, by means of suitable adapter, at a thermostated temperature of 25° C. The invention polymers have values of UL viscosity in the range from 3 cPs to 60 cPs.

Viscosity 0.5% solution: In a suitable becker equipped with mechanical stirring and suitable flat paddle, in order not to "cut" the polymer, a polymeric solution in water by osmosis at 0.5% on polymeric dry basis is prepared. The solution is left under stirring for 30 minutes and then thermostated at 25° C. After thermostatation the viscosity is measured through Brookfield viscometer by means of suitable spindle. The 0.5% viscosities of the new "Acrylamide Free" polymers synthetized in this work were comprised in the range 300 cPs 4000 cPs @ 25° C.

Jar Test: A method widely approved and recognized in the scientific-engineering environment for measuring the flocculating effectiveness of a poly-electrolyte is the Jar Test. A typical apparatus for performing such tests is shown in FIG. 1.

As it can be seen from FIG. 1, the apparatus has 6 flat paddles, connected in parallel, which guarantee the same rotation speed of the sludge to be flocculated. The rotation speed is measured by a suitable tachometer placed high on the instrument.

The stirring paddles will be then placed in 6 beckers, usually 1000-ml beckers, wherein the sludge to be subjected to test (homogenized in advanced) in the extent of 800 gr/becker was placed.

The addition of the poly-electrolyte polymer, in average value from 25 to 100 ppm, was performed when the sludge was subjected to a stirring of about 150 rpm; stronger stirrings could compromise the mechanical stability of the growing floc. One of the beckers is not integrated with the polymer to be analysed and it then remains as "reference" of the performed test. The "acrylamide free" polymers described in this work highlighted optimum performances in the central screening range, that is in the dosages between 50 ppm and 75 ppm.

The flocculation effectiveness in the test was determined both through measurements of transmittance of the aqueous supernatant to the flocculated sludge and through measurements of the dry residue % on the coagulated sludge.

Transmittance Measurement

The transmittance measurements are based upon the selective absorption by molecules of the radiations with wavelength comprised between 200 nm and 780 nm. Such spectral range can be divided into two regions: near UV (200-400 nm) and visible UV (400-780 nm).

Such phenomenon can be exploited to the analytic purposes, by irradiating the sample under examination with a radiation, at known wavelength, with fictitious intensity (Io); then, by detecting the intensity of the emergent radiation (Io−x) the quantity:

$$T = (Io-x)/Io$$

is defined as transmittance.

The water transmittance relatively to a light (UV or visible) ray gives an indication of the limpidity level of the latter.

The greater the water transmittance under examination, the lower the content of impurities which could shield the radiation. Conventionally the water supernatanting the flocculated sludge is analysed at the wavelength of 420 nm; for the white the same water filtered in advance of Whatman membrane Nr. 42 is used. The determinations were performed on UV-VIS spectrophonometer mod. lambda 2 Perkin-Elmer at 420 nm. The new polymers developed herein provided transmittance peaks higher than 90%.

Measurement of the Dry Residue Percentage on the Coagulated Sludge

The dry residue percentage of sludge gives an index of the water purification level, as a sludge with high content of humidity will be index of a difficult separation of the solid phase from the liquid one.

A greater compactness and specific weight of flocs will allow obtaining a more dehydrated sludge outgoing from the plant, thus better separated from water which obviously will go out cleaner and, thanks to a less content of humidity, even with a smaller specific volume. The main component of the produced sludge, in fact, is the water contained in the same with respect to the solid fraction, therefore the volume is wholly constituted by the not separated liquid fraction.

The measurement of the dry residue % is performed on the sludge of the Jar Test. The sludge is collected and drained for 10 minutes on filter 200-μm metallic mesh and then put in furnace at 105° C. for a period of time of 2 hours. Then the % difference in sample weight before and after drying is calculated. The herein described "acrylamide Free" poly-electrolytes, on the average, produced an average value of dry residue percentage higher than 7-8%.

The invention is described hereinafter by means of examples having illustrating and not limitative purpose.

Example 1: Synthesis of a Poly-Cationic Polymer (AF 100 SA) Based Upon Acryloxyethyltrimethyl Ammonium Cchloride (AETAC) With the "A" Synthesis Method Preparation of the oil phase: 461.82 g of paraffinic, desulphurized and de-aromatized solvent are mixed with 20.5 g of mono-oleate Sorbitan and 20.5 g of Oleil-isopranolamine. The mixture is let under stirring until phase homogeneity.

Preparation of the aqueous phase: 1084.30 g of Acryloxyethyltrimethyl Ammonium chloride in 80% aqueous solution are mixed with 353.15 g of water by osmosis, 8.83 g of a solution of 1% Potassium Bromate, 2.50 g of Isopropyl alcohol, 0.70 g of Diethylenetriaminepentaacetic acid sodium salt, 10.00 g di Ammonium Chloride and 0.27 g of Sulphuric Acid to bring the pH of the aqueous solution in the range of 5.00+/−0.2. Then, by means of syringe, a quantity of Cupreous Chloride (dissolved in water) is added, so as to have a final concentration in the emulsion equal to 4 ppm of Cupreous ion. The solution is stirred to have phase homogeneity.

Preparation of the raw emulsion: In order to form properly the raw emulsion to be polymerized in the suitable reactor, the aqueous phase described before is inserted under stirring in the oil phase. After suitable pre-mixing, the two phases are homogenized effectively by means of a highly effective hand homogenizer. When the bulk viscosity of the emulsion reaches a range of 1000-1200 cPs @ 25° C. (viscosity measured by means of Brookfield viscometer) the homogenization is interrupted and the emulsion to be polymerized is placed into the synthesis reactor.

Polymerization reaction: The emulsion to be polymerized is put into a suitable laboratory 3-liter synthesis reactor equipped with: mechanical stirring, micro-peristaltic dosing system, Nitrogen sparge, bubbler and temperature-controlling system. The reactor is then suitably closed and placed under mixing. The emulsion is subjected to a Nitrogen sparge equal to 2 l/m to expel the atmospheric Oxygen which would inhibit polymerization. After 30 minutes of sparge, and without modifying the Nitrogen flow, 1.30 g of a 1% solution of tert-Butyl hydroperoxide are additivated to the reactor. After further 30 minutes of Nitrogen sparge at 2 l/m, the gas flow is decreased to 1 l/m and the emulsion temperature is brought at 25.0° C.

By means of micro-peristaltic dosing system the additivation to the reacting system of a solution of 0.5% Sodium metabisulfite is started, which will trigger the polymerization reaction. The reducing solution will have to be dosed in the emulsion at a dosage so that the reactor temperature passes from 25.0° C. to 37.5° C. in 60 minutes.

Once reached such ideal polymerization temperature, the dosage of reducing solution to the reactor will be optimized during the whole reaction period; solutions with growing concentrations of Sodium metabisulfite (1.0% and 5.0%) could be used during synthesis to guarantee to keep the temperature of 37.5° C.

When even by using the most concentrate reducing solution, it is no more possible to keep the reaction temperature at 37.5° C., this will mean that the final polymerization phase has been reached.

The burn-out: Without interrupting either stirring or Nitrogen sparge, 2.00 g of a 1% solution of tert-Butyl hydroperoxide are then additioned and after 5 minutes 10.00 g of a 30% solution of Sodium metabisulfite; the reaction is then kept at the temperature of 37.5° C., even by heating, for further 60 minutes.

The inversion surfactants: Once the 60 minutes of the previous item have passed, the emulsion is cooled at 25° C. and additivated with 45.90 g of an Alkyl-poly-glycol ether with a HLB 10-12 and 8.10 g of Sodium dioctyl sulphosuccinate. The polymerized and stabilized emulsion is left under stirring for 60 minutes and at last discharged by the reactor.

Example 2: Synthesis of a Poly-Cationic Polymer (AF 100 SB) Based Upon Acryloxyethyltrimethyl Ammonium Chloride With the "B" Synthesis Method Preparation of the oil phase: 461.80 g of paraffinic, desulphurized and de-aromatized solvent are mixed with 20.5 g of Mono-oleate Sorbitan and 20.5 g of Oleil-isopranolamine. The mixture is let under stirring until phase homogeneity.

Preparation of the aqueous phase: 1084.30 g of Acryloxyethyltrimethyl Ammonium chloride in 80% aqueous solution are mixed with 353.15 g of water by osmosis, 8.83 g of a 1% solution of Potassium bromate, 2.50 g of Isopropyl alcohol, 0.70 g of Diethylenetriaminepentaacetic acid sodium salt, 10.00 g of Ammonium Chloride and 0.27 g of Sulphuric Acid to bring the pH of the aqueous solution in the range of 5.00+/−0.2.

The solution is stirred to obtain phase homogeneity.

Preparation of the raw emulsion: In order to form properly the raw emulsion to be polymerized in the suitable reactor, the aqueous phase described before is transferred under stirring into the oil phase. After suitable pre-mixing, the two phases are homogenized effectively by means of a highly effective hand homogenizer. When the bulk viscosity of the emulsion reaches a range of 1000-1200 cPs @ 25° C. (viscosity measured by means of Brookfield viscometer) the homogenization is interrupted and the emulsion to be polymerized is put into the synthesis reactor.

Polymerization reaction: The emulsion to be polymerized is put into a suitable laboratory 3-liter synthesis reactor equipped with: mechanical stirring, micro-peristaltic dosing system, Nitrogen sparge, bubbler and temperature-controlling system. The reactor is suitably closed and placed under mixing. The emulsion is then subjected to a Nitrogen sparge equal to 2 l/m to expel the atmospheric Oxygen which would inhibit polymerization. After 40 minutes of sparge, and without modifying the Nitrogen flow, 2.66 g of a 1% solution of the Wako V 50 catalyst [2,2'-Azobis(2-Methyl-Butyronitrile)] are additivated to the reactor and the heating in the reactor is started which in the following 20 minutes will have to be brought at the reaction temperature of 37.5° C. Once reached 37.5° C. the polymerization reaction will be started and it will be possible to decrease the Nitrogen flow to 1 l/m. Possible additional additions of catalyst with higher concentration could be requested during reaction. When even in front of a further addition of catalyst it is no more possible to keep the reaction temperature at 37.5° C., this will mean that the final polymerization phase has been reached.

The burn-out: Without interrupting either stirring or Nitrogen sparge, 2.00 g of a 1% solution of tert-Butyl hydroperoxide are then additioned and after 5 minutes 10.00 g of a 30% solution of Sodium metabisulfite; the reaction is then kept at the temperature of 37.5° C., even by heating, for further 60 minutes.

The inversion surfactants: Once the 60 minutes of the previous item have passed, the emulsion is cooled at 25° C. and additivated with 45.90 g of an Alkyl-poly-glycol ether with a HLB 10-12 and 8.10 g of Sodium dioctyl sulphosuccinate. The polymerized and stabilized emulsion is left under stirring for 60 minutes and at last discharged by the reactor.

Example 3: Synthesis of a Poly-Anionic Polymer Based Upon Acrylic Acid (AF 100 A SA) with the "A" Synthesis Method Preparation of the oil phase: 354.60 g di paraffinic, desulphurized and de-aromatized solvent are mixed with 20.5 g of Mono-oleate Sorbitan and 20.5 d of Oleil-isopropanolamine. The mixture is let under stirring until phase homogeneity.

Preparation of the aqueous phase: 446.25 g of 99% Acrylic Acid are mixed with 199.00 g of water by osmosis and neutralized with 329.26 g of 32% Ammonia up to a pH 7.5. At last 1.40 g of Diethylenetriaminepentaacetic acid sodium salt and 0.50 g of Isopropyl alcohol are added. Then, by means of syringe, a quantity of Cupreous Chloride (dissolved in water) is added so as to have a final concentration in the emulsion equal to 4 ppm of Cupreous ion. The solution is stirred to obtain phase homogeneity.

Preparation of the raw emulsion: In order to form properly the raw emulsion to be polymerized in the suitable reactor, the aqueous phase described before is transferred under stirring into the oil phase. After suitable pre-mixing, the two phases are homogenized effectively by means of a highly effective hand homogenizer. When the bulk viscosity of the emulsion reaches a range of 1000-1200 cPs @ 25° C. (viscosity measured by means of Brookfield viscometer) the homogenization is interrupted and the emulsion to be polymerized is put into the synthesis reactor.

The polymerization reaction: The emulsion to be polymerized is put into a suitable laboratory 3-liter synthesis reactor equipped with: mechanical stirring, micro-peristaltic dosing system, Nitrogen sparge, bubbler and temperature-controlling system. The reactor then is suitably closed and placed under mixing. The emulsion is subjected to a Nitrogen sparge equal to 2 l/m to expel the atmospheric Oxygen which would inhibit polymerization. After 30 minutes of sparge, and without modifying the Nitrogen flow, 1.30 g of a 1% solution of di tert-Butyl hydroperoxide are additivated to the reactor. After further 30 minutes of Nitrogen sparge at 2 l/m the gas flow is decreased to 1 l/m and the emulsion temperature is brought to 25.0° C. By means of micro-peristaltic dosing system the additivation to the reacting system of a solution of 0.5% Sodium metabisulfite is started, which will trigger the polymerization reaction. The reducing solution will have to be dosed in the emulsion at a dosage so that the reactor temperature passes from 25.0° C. to 37.5° C. in 60 minutes.

Once reached such ideal polymerization temperature, the dosage of reducing solution to the reactor will be optimized during the whole reaction period; solutions with growing concentrations of Sodium metabisulfite (1.0% and 5.0%) could be used during synthesis to guarantee to keep the temperature of 37.5° C.

When even by using the most concentrated reducing solution, it is no more possible to keep the reaction temperature at 37.5° C., this will mean that the final polymerization phase has been reached.

The burn-out: Without interrupting either stirring or Nitrogen sparge, 4.00 g of a 1% solution of tert-Butyl hydroperoxide are then additioned and after 5 minutes 20.00 g of a 30% solution of Sodium metabisulfite; the reaction is then kept at the temperature of 37.5° C., even by heating, for further 60 minutes.

The inversion surfactants: Once the 60 minutes of the previous item have passed, the emulsion is cooled at 25° C. and additivated with 34.85 g of an Alkyl-poly-glycol ether with a HLB 10-12 and 6.15 g of Sodium dioctyl sulphosuccinate. The polymerized and stabilized emulsion is left under stirring for 60 minutes and at last discharged by the reactor.

Example 4: Synthesis of a Poly-Anionic Polymer Based Upon Acrylic Acid (AF 100 A SB) with the "B" Synthesis Method Preparation of the oil phase: 354.60 g of paraffinic, desulphurized and de-aromatized solvent are mixed with 20.5 g of Mono-oleate Sorbitan and 20.5 d of Oleil-isopropanolamine. The mixture is let under stirring until phase homogeneity.

Preparation of the aqueous phase: 446.25 g of 99% Acrylic Acid are mixed with 199.00 g of water by osmosis and neutralized with 329.26 g of 32% Ammonia until a pH 7.5. At last 1.40 g of Diethylenetriaminepentaacetic acid sodium salt and 0.50 g of Isopropyl alcohol are added. The solution is stirred to obtain phase homogeneity.

Preparation of the raw emulsion: In order to form properly the raw emulsion to be polymerized in the suitable reactor, the aqueous phase described before is transferred under stirring into the oil phase. After suitable pre-mixing, the two phases are homogenized effectively by means of a highly effective hand homogenizer. When the bulk viscosity of the emulsion reaches a range of 1000-1200 cPs @ 25° C. (viscosity measured by means of Brookfield viscometer) the homogenization is interrupted and the emulsion to be polymerized is put into the synthesis reactor.

The polymerization reaction: The emulsion to be polymerized is put into a suitable laboratory 3-liter synthesis reactor equipped with: mechanical stirring, micro-peristaltic dosing system, Nitrogen sparge, bubbler and temperature-controlling system. The reactor is closed and placed under mixing. The emulsion then is subjected to a Nitrogen sparge equal to 2 l/m to expel the atmospheric Oxygen which would inhibit polymerization. After 40 minutes of sparge, and without modifying the Nitrogen flow, 2.66 g of a 1% solution of the Wako V 50 catalyst [2,2'-Azobis(2-Methyl-Butyronitrile)] are additivated to the reactor and the heating in the reactor is started which in the following 20 minutes will have to be brought at the reaction temperature of 37.5° C. Once reached 37.5° C. the polymerization reaction will be started and it will be possible to decrease the Nitrogen flow to 1 l/m. Possible further additions of catalyst with higher concentration could be requested during reaction.

When even in front of a further addition of catalyst it is no more possible to keep the reaction temperature at 37.5° C., this will mean that the final polymerization phase has been reached.

The burn-out: Without interrupting either stirring or Nitrogen sparge, 2.00 g of a 1% solution of tert-Butyl hydroperoxide are then additioned and after 5 minutes 10.00 g of a 30% solution of Sodium metabisulfite; the reaction is then kept at the temperature of 37.5° C., even by heating, for further 60 minutes.

The inversion surfactants: Once the 60 minutes of the previous item have passed, the emulsion is cooled at 25° C. and additivated with 34.85 g of an Alkyl-poly-glycol ether with a HLB 10-12 and 6.15 g of Sodium dioctyl sulphosuccinate. The polymerized and stabilized emulsion is left under stirring for 60 minutes and at last discharged by the reactor.

Example 5: Synthesis of a Poly-Zwitterionic Polymer (QZ 271 SA) Based Upon Acryloxyethyltrimethyl Ammonium Chloride and Acrylic Acid (50:50 w/w as Polymeric Active) with the "A" Synthesis Method Preparation of the oil phase: 504.00 g of paraffinic, desulphurized and de-aromatized solvent are mixed with 20.00 g of Mono-oleate Sorbitan and 20.00 d of Oleil-isoprapanolamine. The mixture is let under stirring until phase homogeneity.

Preparation of the aqueous phase: 370.33 g of Acryloxyethyltrimethyl Ammonium chloride in 80% aqueous solution and 296.26 g of 99% Acrylic Acid are mixed with 420.62 g of water by osmosis and are neutralized at pH 7.50 with 218.59 g of 32% Ammonia. 12.00 g of a 1% solution of Potassium bromate, 1.84 g of Isopropyl alcohol, 1.12 g of Diethylenetriaminepentaacetic acid sodium salt and 25.20 g of Ammonium Sulfate are then additioned to the solution. Then, by means of syringe, a quantity of Cupreous Chloride (dissolved in water) is added so as to have a final concentration in the emulsion equal to 4 ppm of Cupreous ion. The solution is stirred to obtain phase homogeneity.

Preparation of the raw emulsion: In order to form properly the raw emulsion to be polymerized in the suitable reactor, the aqueous phase described before is transferred under stirring into the oil phase. After suitable pre-mixing, the two phases are homogenized effectively by means of a highly effective hand homogenizer. When the bulk viscosity of the emulsion reaches a range of 1000-1200 cPs @ 25° C. (viscosity measured by means of Brookfield viscometer) the homogenization is interrupted and the emulsion to be polymerized is put into the synthesis reactor.

The polymerization reaction: The emulsion to be polymerized is put into a suitable laboratory 3-liter synthesis reactor equipped with: mechanical stirring, micro-peristaltic dosing system, Nitrogen sparge, bubbler and temperature-controlling system. The reactor then is suitably closed and placed under mixing. The emulsion is subjected to a Nitrogen sparge equal to 2 l/m to expel the atmospheric Oxygen which would inhibit polymerization. After 30 minutes of sparge, and without modifying the Nitrogen flow, 0.40 g of a 1% solution of di tert-Butyl hydroperoxide are additivated to the reactor. After further 30 minutes of Nitrogen sparge at 2 l/m the gas flows is decreased to 1 l/m and the emulsion temperature is brought to 25.0° C.

By means of micro-peristaltic dosing system the additivation to the reacting system of a solution of 0.5% Sodium metabisulfite is started, which will trigger the polymerization reaction. The reducing solution will have to be dosed in the emulsion at a dosage so that the reactor temperature passes from 25.0° C. to 37.5° C. in 60 minutes.

Once reached such ideal polymerization temperature, the dosage of reducing solution to the reactor will be optimized during the whole reaction period; solutions with growing concentrations of Sodium metabisulfite (1.0% and 5.0%) could be used during synthesis to guarantee to keep the temperature of 37.5° C.

When even by using the most concentrated reducing solution, it is no more possible to keep the reaction temperature at 37.5° C., this will mean that the final polymerization phase has been reached.

The burn-out: Without interrupting either stirring or Nitrogen sparge, 2.00 g of a 1% solution of tert-Butyl hydroperoxide are then additioned and after 5 minutes 10.00 g of a 30% solution of Sodium metabisulfite; the reaction is then kept at the temperature of 37.5° C., even by heating, for further 60 minutes.

The inversion surfactants: Once the 60 minutes of the previous item have passed, the emulsion is cooled at 25° C. and additivated with 46.75 g of an Alkyl-poly-glycol ether with a HLB 10-12 and 8.25 g of Sodium dioctyl sulphosuccinate. The polymerized and stabilized emulsion is left under stirring for 60 minutes and at last discharged by the reactor.

Example 6: Synthesis of a Poly-Zwitterionic Polymer (QZ 271 SB) Based Upon Acryloxyethyltrimethyl Ammonium Chloride and Acrylic Acid (50:50 w/w as Polymeric Active) With the "B" Synthesis Method Preparation of the oil phase: 504.00 g of paraffinic, desulphurized and de-aromatized solvent are mixed with 20.00 g of Mono-oleate Sorbitan and 20.00 d of Oleil-isoprapanolamine. The mixture is let under stirring until phase homogeneity.

Preparation of the aqueous phase: 370.33 g of Acryloxyethyltrimethyl Ammonium chloride in 80% aqueous solution and 296.26 g of 99% Acrylic Acid are mixed with 420.62 g of water by osmosis and are neutralized at pH 7.50 with 218.59 g of 32% Ammonia. 12.00 g of a 1% solution of Potassium bromate, 1.84 g of Isopropyl alcohol, 1.12 g of Diethylenetriaminepentaacetic acid sodium salt and 25.20 g of Ammonium Sulfate are then additioned to the solution. The solution is stirred to obtain phase homogeneity.

Preparation of the raw emulsion: In order to form properly the raw emulsion to be polymerized in the suitable reactor, the aqueous phase described before is transferred under stirring into the oil phase. After suitable pre-mixing, the two phases are homogenized effectively by means of a highly effective hand homogenizer. When the bulk viscosity of the emulsion reaches a range of 1000-1200 cPs @ 25° C. (viscosity measured by means of Brookfield viscometer) the homogenization is interrupted and the emulsion to be polymerized is put into the synthesis reactor.

The polymerization reaction: The emulsion to be polymerized is put into a suitable laboratory 3-liter synthesis reactor equipped with: mechanical stirring, micro-peristaltic dosing system, Nitrogen sparge, bubbler and temperature-controlling system. The reactor is suitably closed and placed under mixing. The emulsion then is subjected to a Nitrogen sparge equal to 2 l/m to expel the atmospheric Oxygen which would inhibit polymerization. After 40 minutes of sparge, and without modifying the Nitrogen flow, 2.06 g of a 1% solution of the Wako V 50 catalyst [2,2'-Azobis(2-MethylButyronitrile)] are additivated to the reactor and the heating in the reactor is started which in the following 20 minutes will have to be brought at the reaction temperature of 37.5° C. Once reached 37.5° C. the polymerization reaction will be started and it will be possible to decrease the Nitrogen flow to 1 l/m. Possible further additions of catalyst with higher concentration could be requested during reaction.

When even in front of a further addition of catalyst it is no more possible to keep the reaction temperature at 37.5° C., this will mean that the final polymerization phase has been reached.

The burn-out: Without interrupting either stirring or Nitrogen sparge, 2.00 g of a 1% solution of tert-Butyl hydroperoxide are then additionated and after 5 minutes 10.00 g of a 30% solution of Sodium metabisulfite; the reaction is then kept at the temperature of 37.5° C., even by heating, for further 60 minutes.

The inversion surfactants: Once the 60 minutes of the previous item have passed, the emulsion is cooled at 25° C. and additivated with 46.75 g of an Alkyl-poly-glycol ether with a HLB 10-12 and 8.25 g of Sodium dioctyl sulphosuccinate. The polymerized and stabilized emulsion is left under stirring for 60 minutes and at last discharged by the reactor.

The features of the linear polymers synthetized above are shown in Table 3.

reactor equipped with: mechanical stirring, micro-peristaltic dosing system, Nitrogen sparge, bubbler and temperature-controlling system. The reactor then is suitably closed and placed under mixing. The emulsion is subjected to a Nitrogen sparge equal to 2 l/m to expel the atmospheric Oxygen which would inhibit polymerization. After 30 minutes of sparge, and without modifying the Nitrogen flow, 1.30 g of a 1% solution of di tert-Butyl hydroperoxide are additivated to the reactor. After further 30 minutes of Nitrogen sparge at 2 l/m the gas flows is decreased to 1 l/m and the emulsion temperature is brought to 25.0° C. By means of micro-peristaltic dosing system the additivation to the reacting system of a solution of 0.5% Sodium metabisulfite is started,

TABLE 3

|  | AF 100 SA | AF 100 SB | AF 100 A SA | AF 100 A SB | QZ 271 SA | QZ 271 SB |
|---|---|---|---|---|---|---|
| Appearance | O.E. | O.E. | O.E. | O.E. | O.E. | O.E. |
| Bulk Viscosity (cPs @ 25° C.) | 2150 | 1700 | 1350 | 1250 | 1400 | 1350 |
| (1) UL Viscosity (cPs @ 25° C.) | 10.7 | 14.5 | 49.8 | 55.2 | 13.1 | 14.5 |
| Solids % (w/w) | 47.33 | 46.62 | 38.49 | 39.15 | 39.14 | 39.99 |
| (2) 0.5% solution viscosity (cPs @ 25° C.) | 1450 | 1600 | 4120 | 4250 | 490 | 600 |
| Dissolution Test (s) | 3 | 1 | 3 | 2 | 10 | 8 |
| Free monomer (ppm) | <50 | <50 | <50 | <50 | <50 | <50 |
| Gels % (w/w) | <0.2 | <0.2 | <0.2 | <0.2 | <0.2 | <0.2 |

Legend: O.E. = Opaque emulsion;
(1) based on dry polymer;
(2) based on dry polymer

Example 7: Synthesis of a Cross-Linked Poly-Cationic Polymer (AF 100 SA 3 CL) Based Upon Acryloxyethyltrimethyl Ammonium Chloride Cross-Linked (CL) With 3 ppm of Methylene Bisacrylamide With the "A" Synthesis Method Preparation of the oil phase: 461.82 g of paraffinic, desulphurized and de-aromatized solvent are mixed with 20.5 g of Mono-oleate Sorbitan and 20.5 d of Oleil-isopranolamine. The mixture is let under stirring until phase homogeneity.

Preparation of the aqueous phase: 1084.30 g of Acryloxyethyltrimethyl Ammonium chloride in 80% aqueous solution are mixed with: 353.15 g of water by osmosis, 8.83 g of a 1% solution of Potassium bromate, 1.50 g of Isopropyl alcohol, 0.70 g of Diethylenetriaminepentaacetic acid sodium salt, 10.00 g of Ammonium Chloride, 6.00 g of a 0.1% aqueous solution of Methylene bisacrylamide and 0.27 g of Sulphuric Acid to bring the pH of the aqueous solution in the range of 5.00+/−0.2. Then, by means of a syringe, a quantity of Cupreous Chloride (dissolved in water) is added, so as to have a final concentration in the emulsion equal to 4 ppm of Cupreous ion. The solution is stirred to obtain phase homogeneity.

Preparation of the raw emulsion: In order to form properly the raw emulsion to be polymerized in the suitable reactor, the aqueous phase described before is transferred under stirring into the oil phase. After suitable pre-mixing, the two phases are homogenized effectively by means of a highly effective hand homogenizer. When the bulk viscosity of the emulsion reaches a range of 1000-1200 cPs @ 25° C. (viscosity measured by means of Brookfield viscometer) the homogenization is interrupted and the emulsion to be polymerized is put into the synthesis reactor.

The polymerization reaction: The emulsion to be polymerized is put into a suitable laboratory 3-liter synthesis which will trigger the polymerization reaction. The reducing solution will have to be dosed in the emulsion at a dosage so that the reactor temperature passes from 25.0° C. to 37.5° C. in 60 minutes. Once reached such ideal polymerization temperature, the dosage of reducing solution to the reactor will be optimized during the whole reaction period; solutions with growing concentrations of Sodium metabisulfite (1.0% and 5.0%) could be used during synthesis to guarantee to keep the temperature of 37.5° C.

When even by using the most concentrated reducing solution, it is no more possible to keep the reaction temperature at 37.5° C., this will mean that the final polymerization phase has been reached.

The burn-out: Without interrupting either stirring or Nitrogen sparge, 2.00 g of a 1% solution of tert-Butyl hydroperoxide are then additionated and after 5 minutes 10.00 g of a 30% solution of Sodium metabisulfite; the reaction is then kept at the temperature of 37.5° C., even by heating, for further 60 minutes.

The inversion surfactants: Once the 60 minutes of the previous item have passed, the emulsion is cooled at 25° C. and additivated with 45.90 g of an Alkyl-poly-glycol ether with a HLB 10-12 and 8.10 g of Sodium dioctyl sulphosuccinate. The polymerized and stabilized emulsion is left under stirring for 60 minutes and at last discharged by the reactor.

Example 8: Synthesis of the Polymers Cross-Linked at 3 Ppm of CLC and 6 Ppm of CLC of the Polymers Shown in Table 3

By operating under the same conditions described in example 7, the versions cross-linked at 3 ppm of CLC and 6 ppm of CLC of the polymers shown in table 3 were then synthetized.

The polymers cross-linked at 3 ppm of CLC are shown in table 4, whereas those at 6 ppm of CLC are shown in table 5.

TABLE 4

CLC at 3 ppm

|  | AF 100 SA 3 CLC | AF 100 SB 3 CLC | AF 100 A SA 3 CLC | AF 100 A SB 3 CLC | QZ 271 SA 3 CLC | QZ 271 SB 3 CLC |
|---|---|---|---|---|---|---|
| Appearance | O.E. | O.E. | O.E. | O.E. | O.E. | O.E. |
| Bulk Viscosity (cPs @ 25° C.) | 2170 | 1980 | 1392 | 1420 | 804 | 904 |
| (1) UL Viscosity (cPs @ 25° C.) | 12 | 12.5 | 10.8 | 11.6 | 12.3 | 12.7 |
| Solids % (w/w) | 47.17 | 46.88 | 38.89 | 39.01 | 33.61 | 34.1 |
| (2) 0.5% solution viscosity (cPs @ 25° C.) | 1850 | 1910 | 5700 | 5800 | 330 | 350 |
| Dissolution Test (s) | 2 | 2 | 2 | 2 | 15 | 14 |
| Free monomer (ppm) | <50 | <50 | <50 | <50 | <50 | <50 |
| Gels % (w/w) | 0.2 | 0.25 | 0.1 | 0.3 | 0.1 | 0.2 |

Legend: O.E. = Opaque emulsion;
(1) based on dry polymer;
(2) based on dry polymer

TABLE 5

CLC at 6 ppm

|  | AF 100 SA 6 CLC | AF 100 SB 6 CLC | AF 100 A SA 6 CLC | AF 100 A SB 6 CLC | QZ 271 SA 6 CLC | QZ 271 SB 6 CLC |
|---|---|---|---|---|---|---|
| Appearance | O.E. | O.E. | O.E. | O.E. | O.E. | O.E. |
| Bulk Viscosity (cPs @ 25° C.) | 2100 | 1980 | 1280 | 1420 | 1992 | 1840 |
| (1) UL Viscosity (cPs @ 25° C.) | 9.2 | 9.15 | 5.9 | 6.1 | 12.3 | 12.1 |
| Solids % (w/w) | 46.67 | 47.01 | 37.36 | 38.15 | 36.44 | 37.02 |
| (2) 0.5% solution viscosity (cPs @ 25° C.) | 1900 | 1850 | 8950 | 8700 | 310 | 330 |
| Dissolution Test (s) | 2 | 2 | 2 | 2 | 14 | 13 |
| Free monomer (ppm) | <50 | <50 | <50 | <50 | <50 | <50 |
| Gels % (w/w) | 0.15 | 0.2 | 0.2 | 0.4 | 0.2 | 0.2 |

Legend: O.E. = Opaque emulsion;
(1) based on dry polymer;
(2) based on dry polymer (Application) Example 9: Application of the Polymers of the Invention The products synthetized and shown in tables 3, 4 and 5 were used as flocculating agents on a type sludge to measure the performances thereof. The sludge used for the tests is characterized in table 6.

TABLE 6

Features of the sludge used in the tests "Acrylamide Free" poly-electrolyte performance - average sludge characteristics used for the tests

| Parameter | Note | Result | Unit | Range |
|---|---|---|---|---|
| pH |  | 7.6 | " | 7.5-8.20 |
| Color | Red/Brown | Pass | " | " |
| Odour | Mossy | Pass | " | " |
| Settleable solids | Imhoff cone 30 m | 230 | ml/l | <250 |
| Total suspended solids (TSS) | Filtration on 0.45 μm (105° C.) | 6.5 | g/l | 5-7 |
| Volatile suspended solids (VSS) | 600° C. × 1 h | 4.5 | g/l | ~70% TSS |
| Fixed suspended solids (FSS) | 600° C. × 1 h | 1.6 | g/l | 1-3 |
| Umidity | 105° C. | 93.5 | % | " |
| Character | " | Anphoteric | mg/l | " |
| Sodium | " | 31.154 | mg/l | " |
| Potassium | " | 30.542 | mg/l | " |
| Magnesium | " | 15.468 | mg/l | " |
| Silica | " | 74.893 | mg/l | " |
| Calcium | " | 315.272 | mg/l | " |
| Iron | " | 2.569 | mg/l | " |
| Manganese | " | 0.145 | mg/l | " |
| Nickel | " | 1.023 | mg/l | " |
| Lead | " | 9.112 | mg/l | " |
| Copper | " | 0.05 | mg/l | " |
| Mercury | " | 0.001 | mg/l | " |

The methods used to measure the effectiveness of the synthetized polymers (i.e. transmittance of the supernatant and residual humidity percentage of the coagulated sludge) are described in the section "Experimental portion and analytical methods" of the present application (above).

The invention polymers used in the application examples are:

AF 100 SA (example 1); AF 100 SB (example 2); AF 100 SA 3CL (example 7); AF 100 SB 3 CL (example 8); AF 100 SA 6 CL (example 8); AF 100 SB 6 CL (example 8).

These invention polymers were put in comparison with acrylamide-based commercial polymers:

QUALIFOC CE 2040, Acrylamide/AETAC (60/40% in moles) linear copolymer, currently commercialized by GRS and QUALIFOC CL 7040, Acrylamide/AETAC (60/40% in moles) cross-linked copolymer, currently commercialized by GRS.

The flocculation pH of the sludge was fixed in the range of 7.00+/−0.2 for all the used polymers.

Figure 2:
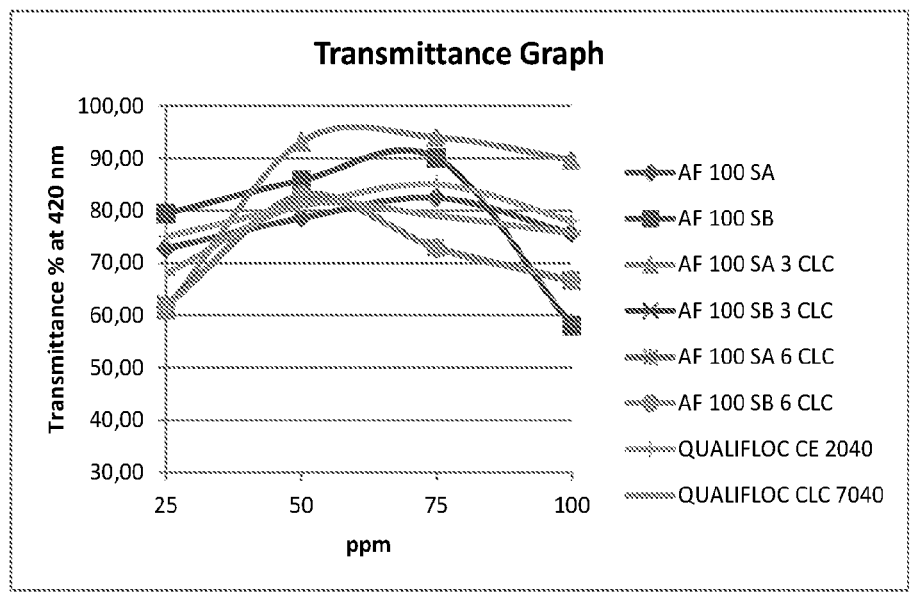
FIG. 2: the figure includes two graphs illustrating the results shown in Table 7. Graph 1 represents the Transmittance of purified water with the cationic polymers; Graph 2 shows the dry Residue % in the sludge treated with the cationic polymers.
Figure 2:
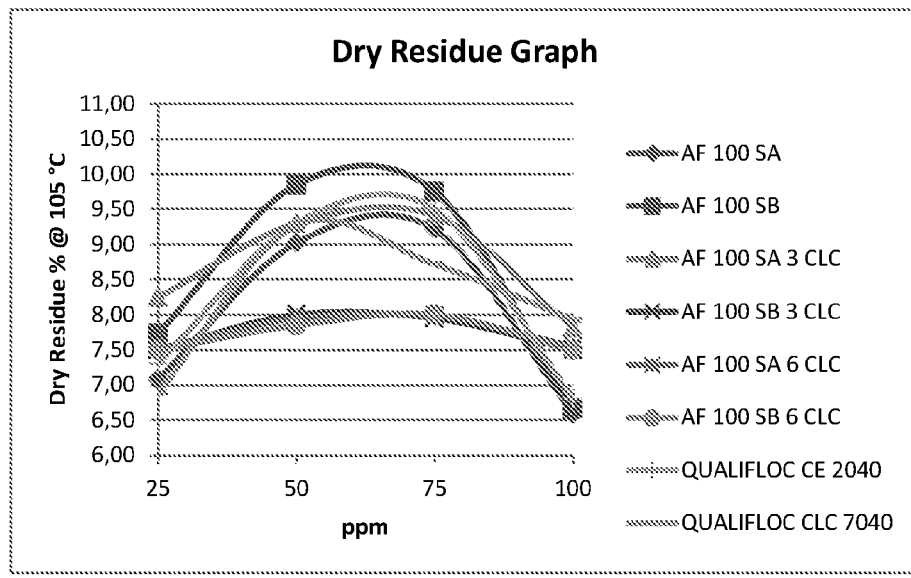

The obtained results are shown in table 7. The graphs 1 and 2 (FIG. 2) are a graphic representation of the results.

TABLE 7

Cationic polymers performance

| Polymer name | ppm | | | | | | | |
|---|---|---|---|---|---|---|---|---|
| | 25 | 50 | 75 | 100 | 25 | 50 | 75 | 100 |
| AF 100 SA | 72.75 | 78.57 | 82.45 | 75.66 | 7.08 | 9.02 | 9.22 | 6.60 |
| AF 100 SB | 79.43 | 85.78 | 90.02 | 58.00 | 7.73 | 9.85 | 9.75 | 6.66 |
| AF 100 SA 3 CLC | 61.15 | 93.15 | 94.00 | 89.70 | 8.25 | 9.30 | 9.41 | 7.82 |
| AF 100 SB 3 CLC | 62.00 | 82.50 | 73.00 | 66.50 | 7.50 | 8.00 | 7.95 | 7.50 |
| AF 100 SA 6 CLC | 61.80 | 82.30 | 73.00 | 66.70 | 7.52 | 7.95 | 7.98 | 7.55 |
| AF 100 SB 6 CLC | 61.70 | 83.00 | 72.80 | 66.70 | 7.50 | 7.85 | 8.00 | 7.50 |
| QUALIFLOC CE 2040 | 75.00 | 81.00 | 85.00 | 78.00 | 7.30 | 9.30 | 9.50 | 6.80 |
| QUALIFLOC CLC 7040 | 68.00 | 81.00 | 79.00 | 75.70 | 6.89 | 9.27 | 8.72 | 7.93 |
| | Transmittance at 420 nm | | | | Dry residue (w/w %) | | | |

Figure 3:
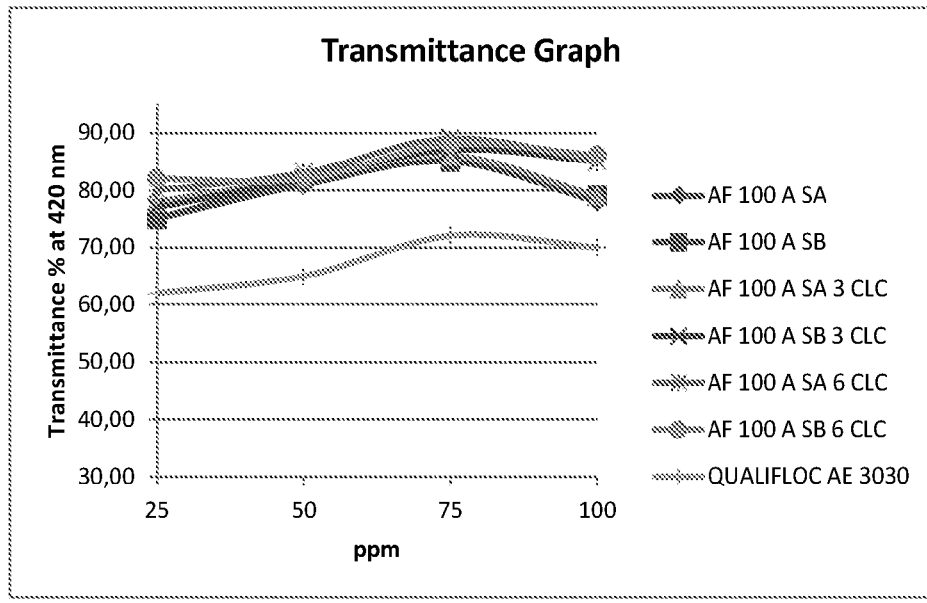
FIG. 3: the figure includes two graphs illustrating the results shown in Table 8. Graph 3—represents the Transmittance of purified water with the anionic polymers. Graph 4 represents the dry Residue % in the sludge treated with the anionic polymers.
Figure 3:
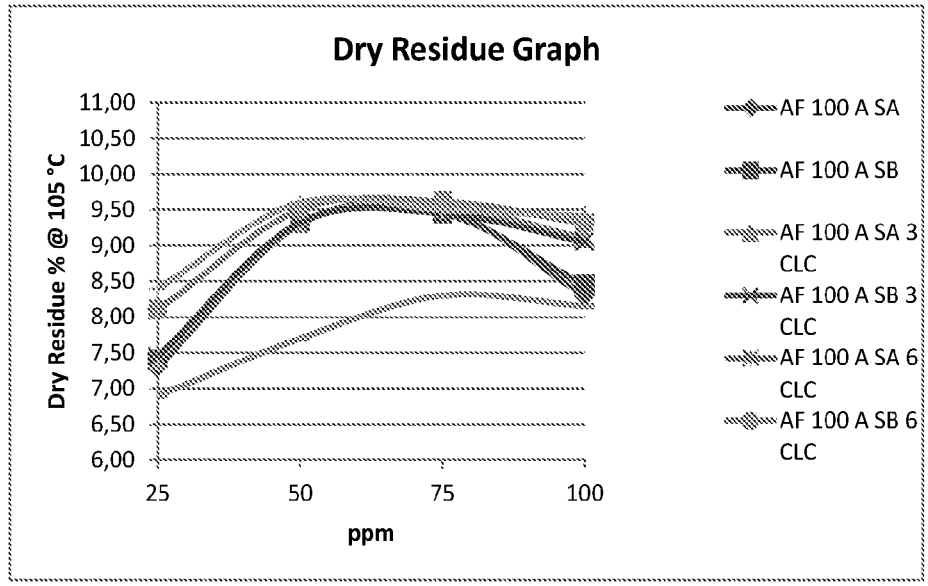

Table 8 shows the results obtained with the anionic polymers wherein, as reference standard, the QUALIFOC AE 3030, Acrylamide/Acrylic Acid (70/30% in moles) linear copolymer, currently commercialized by GRS, was used. The graphs 3 and 4 (FIG. 3) are a visual representation of the results.

TABLE 8

Anionic polymers performance

| Polymer name | ppm | | | | | | | |
|---|---|---|---|---|---|---|---|---|
| | 25 | 50 | 75 | 100 | 25 | 50 | 75 | 100 |
| AF 100 A SA | 75.00 | 81.00 | 85.00 | 78.00 | 7.30 | 9.30 | 9.50 | 8.30 |
| AF 100 A SB | 75.00 | 82.00 | 85.00 | 79.00 | 7.40 | 9.32 | 9.45 | 8.45 |
| AF 100 A SA 3 CLC | 78.00 | 82.00 | 86.00 | 79.00 | 7.40 | 9.31 | 9.54 | 9.10 |
| AF 100 A SB 3 CLC | 77.00 | 82.00 | 87.00 | 85.00 | 7.45 | 9.32 | 9.45 | 9.05 |
| AF 100 A SA 6 CLC | 80.00 | 83.00 | 89.00 | 85.00 | 8.10 | 9.50 | 9.62 | 9.31 |
| AF 100 A SB 6 CLC | 82.00 | 82.00 | 88.00 | 86.00 | 8.40 | 9.60 | 9.50 | 9.41 |
| QUALIFLOC AE 3030 | 62.00 | 65.00 | 72.00 | 70.00 | 6.90 | 7.70 | 8.30 | 8.15 |
| | Transmittance at 420 nm | | | | Dry residue (w/w %) | | | |

Figure 4:
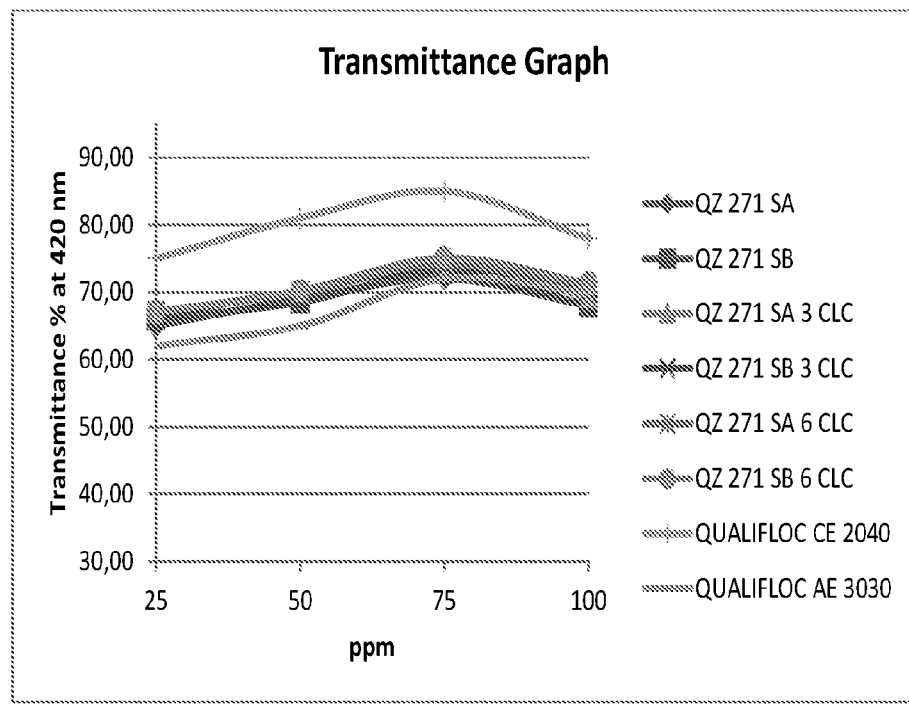
FIG. 4: the figure includes two graphs illustrating the results shown in Table 9. Graph 5 represents the Transmittance of purified water with the zwitterionic polymers. Graph 6 represents the dry Residue % in the sludge treated with the zwitterionic polymers.
Figure 4:
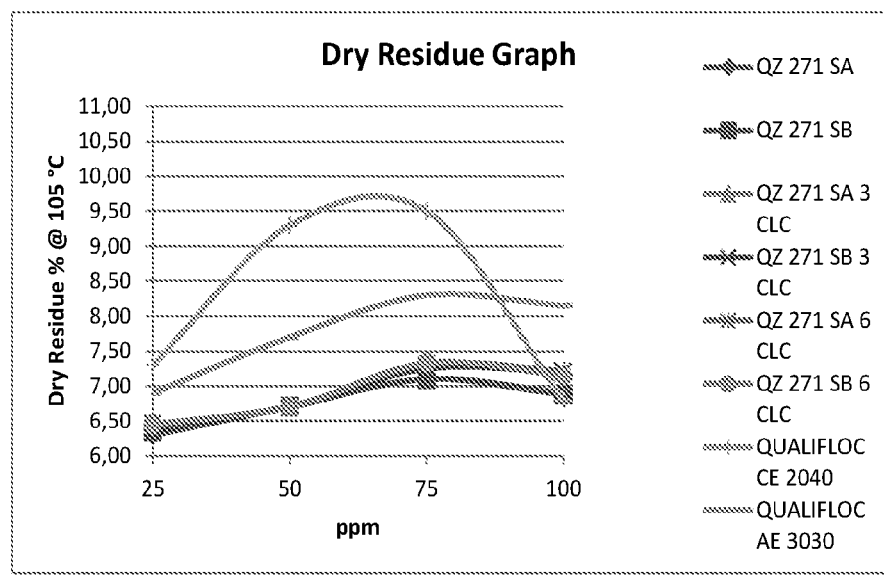

Table 9 shows the results obtained with the zwitterionic polymers wherein, as reference standard, the QUALIFOC AE 3030, Acrylamide/Acrylic Acid (70/30% in moles) linear copolymer, currently commercialized by GRS and the Qualifloc CE 2040 Acrylamide/AETAC (60/40% in moles) linear copolymer, currently commercialized by GRS were used. The graphs 5 and 6 (FIG. 4) are a visual representation of the results.

TABLE 9

Zwitterionic polymers performance

| Polymer name | ppm | | | | | | | |
|---|---|---|---|---|---|---|---|---|
| | 25 | 50 | 75 | 100 | 25 | 50 | 75 | 100 |
| QZ 271 SA | 65.00 | 69.00 | 72.00 | 68.00 | 6.30 | 6.70 | 7.10 | 6.90 |
| QZ 271 SB | 66.00 | 68.50 | 73.00 | 68.00 | 6.35 | 6.71 | 7.10 | 6.88 |
| QZ 271 SA 3 CLC | 67.00 | 70.15 | 74.20 | 69.30 | 6.40 | 6.75 | 7.30 | 7.10 |
| QZ 271 SB 3 CLC | 66.80 | 70.00 | 73.90 | 70.10 | 6.35 | 6.70 | 7.25 | 7.20 |
| QZ 271 SA 6 CLC | 67.00 | 69.99 | 74.20 | 70.20 | 6.45 | 6.71 | 7.31 | 7.22 |
| QZ 271 SB 6 CLC | 67.10 | 70.20 | 75.10 | 71.30 | 6.45 | 6.70 | 7.33 | 7.15 |
| QUALIFLOC CE 2040 | 75.00 | 81.00 | 85.00 | 78.00 | 7.30 | 9.30 | 9.50 | 6.80 |
| QUALIFLOC AE 3030 | 62.00 | 65.00 | 72.00 | 70.00 | 6.90 | 7.70 | 8.30 | 8.15 |
| | Transmittance at 420 nm | | | | Dry residue (w/w %) | | | |

As it can be seen, the invention polymers, when used at the usual concentrations from 25 to 75 ppm, are able to conjugate the advantage of eliminating the acrylamidic monomer, with a flocculation effectiveness always comparable, sometimes even better, to that offered by the acrylamide-based commercial products. In each case the demonstrated effectiveness can be accepted for an industrial application.

Comparative Examples

Four "Acrylamide free" polymers, two anionic and two cationic ones, were synthetized under the usual polymerization conditions in the preparation of anionic/cationic polyacrilamidic polymers: that is at the temperature of 55° C., and by using great quantities of catalyst:
Anionic Polymers:
AF 100 A SCA, based upon Acrylic Acid, wherein "SCA" means: Acrylamide Conventional Synthesis;
AF 100 AM SCA, based upon Methacrylic Acid;
The two monomers were selected based upon the strong structural homology with the Acrylamide monomer.
Cationic Polymers:
AF 100 SCA, based upon AETAC (see table 1).
AF 100 M SCA, based upon METAC (see table 1).
The features of the "Acrylamide free" polymers were compared to those of the acrylamide-based classic polymers.
Anionic Polymers:
Qualifloc AE 3030, Acrylamide/Acrylic Acyd (70/30% in moles) copolymer.
Qualifloc AE 3030 M, Acrylamide/Methacrylic Acid (70/30% in moles) copolymer.
Cationic Polymers:
Qualifloc CE 2040, Acrylamide/AETAC (60/40% in moles) copolymer.
Qualifloc CE 2040 M, Acrylamide/METAC (60/40% in moles) copolymer.

(Comparative) Example 10: Synthesis of a Poly-Anionic Polymer (AF 100 A SCA) Based Upon Acrylic Acid with the "A" Synthesis Method but by Using a Reaction Temperature for the Acrylamide-Based Products Preparation of the oil phase: 354.60 g of paraffinic, desulphurized and de-aromatized solvent are mixed with 20.5 g of Mono-oleate Sorbitan and 20.5 d of Oleil-isopranolamine. The mixture is let under stirring until phase homogeneity.

Preparation of the aqueous phase: 446.25 g of 99% Acrylic Acid are mixed with 199.00 g of water by osmosis and neutralized with 329.26 g of 32% Ammonia up to pH 7.5. At last, 1.40 g of Diethylenetriaminepentaacetic acid sodium salt and 0.50 g of Isopropyl alcohol are added. Then, by means of syringe, a quantity of Cupreous Chloride (dissolved in water) is added so as to have a final concentration in the emulsion equal to 4 ppm of Cupreous ion. The solution is stirred to obtain phase homogeneity.

Preparation of the raw emulsion: one acts under the same conditions described in example 1.

The polymerization reaction: The emulsion to be polymerized is put into a suitable laboratory 3-liter synthesis reactor equipped with: mechanical stirring, micro-peristaltic dosing system, Nitrogen sparge, bubbler and temperature-controlling system. The reactor then is suitably closed and placed under mixing. The emulsion is subjected to a Nitrogen sparge equal to 2 l/m to expel the atmospheric Oxygen which would inhibit polymerization. After 30 minutes of sparge, and without modifying the Nitrogen flow, 2.00 g of a 1% solution of di tert-Butyl hydroperoxide are additivated to the reactor. After further 30 minutes of Nitrogen sparge at 2 l/m the gas flows is decreased to 1 l/m and the emulsion temperature is brought to 25.0° C.

By means of micro-peristaltic dosing system the additivation to the reacting system of a solution of 0.5% Sodium metabisulfite is started, which will trigger the polymerization reaction. The reducing solution will have to be dosed in the emulsion at a dosage so that the reactor temperature passes from 25.0° C. to 55° C. in 30 minutes.

Once reached such ideal polymerization temperature, the dosage of reducing solution to the reactor will be optimized during the whole reaction period; solutions with growing concentrations of Sodium metabisulfite (1.0% and 5.0%) could be used during synthesis to guarantee to keep the temperature of 55° C.

When even by using the most concentrated reducing solution, it is no more possible to keep the reaction temperature at 55° C., this will mean that the final polymerization phase has been reached.

The burn-out: Without interrupting either stirring or Nitrogen sparge, 4.00 g of a 1% solution of tert-Butyl hydroperoxide are then additioned and after 5 minutes 20.00 g of a 30% solution of Sodium metabisulfite; the reaction is then kept at the temperature of 45° C., even by heating, for further 60 minutes.

The inversion surfactants: Once the 60 minutes of the previous item have passed, the emulsion is cooled at 25° C. and additivated with 34.85 g of an Alkyl-poly-glycol ether with a HLB 10-12 and 6.15 g of Sodium dioctyl sulphosuccinate. The polymerized and stabilized emulsion is left under stirring for 60 minutes and at last discharged by the reactor.

(Comparative) Example 11: Synthesis of a Poly-Anionic Polymer (AF 100 AM SCA) Based Upon Methacrylic Acid with the "A" Synthesis Method but by Using a Reaction Temperature for the Acrylamide-Based Products Preparation of the oil phase: 354.60 g of paraffinic, desulphurized and de-aromatized solvent are mixed with 20.5 g of Mono-oleate Sorbitan and 20.5 d of Oleil-isopranolamine. The mixture is let under stirring until phase homogeneity.

Preparation of the aqueous phase: 532.72 g of 99% Methacrylic Acid are mixed with 199.00 g of water by osmosis and neutralized with 329.26 g of 32% Ammonia until pH 7.5. At last 1.40 g of Diethylenetriaminepentaacetic acid sodium salt and 0.50 g of Isopropyl alcohol are added. Then, by means of syringe, a quantity of Cupreous Chloride (dissolved in water) is added, so as to have a final concentration in the emulsion equal to 4 ppm of Cupreous ion. The solution is stirred to obtain phase homogeneity.

Preparation of the raw emulsion: one acts under the same conditions described in the previous example.

The polymerization reaction: one acts under the same conditions described in the previous example.

The burn-out: Without interrupting either stirring or Nitrogen sparge, 4.00 g of a 1% solution of tert-Butyl hydroperoxide are then additioned and after 5 minutes 18.00 g of a 30% solution of Sodium metabisulfite; the reaction is then kept at the temperature of 45° C., even by heating, for further 60 minutes.

The inversion surfactants: Once the 60 minutes of the previous item have passed, the emulsion is cooled at 25° C.

and additivated with 34.85 g of an Alkyl-poly-glycol ether with a HLB 10-12 and 6.15 g of Sodium dioctyl sulphosuccinate. The polymerized and stabilized emulsion is left under stirring for 60 minutes and at last discharged by the reactor.

(Comparative) Example 12: Synthesis of a Poly-Cationic Polymer (AF 100 SCA) Based Upon Acryloxyethyltrimethyl Ammonium Chloride (AETAC) with the "A" Synthesis Method but by Using a Reaction Temperature for the Acrylamide-Based Products Preparation of the oil phase: 461.82 g of paraffinic, desulphurized and de-aromatized solvent are mixed with 20.5 g of Mono-oleate Sorbitan and 20.5 g of Oleil-isopranolamine. The mixture is let under stirring until phase homogeneity.

Preparation of the aqueous phase: 1084.30 g of Acryloxyethyltrimethyl Ammonium chloride in 80% aqueous solution are mixed with 353.15 g of water by osmosis, 8.83 g of a 1% solution of Potassium bromate, 2.50 g of Isopropyl alcohol, 0.70 g of Diethylenetriaminepentaacetic acid sodium salt, 10.00 g of Ammonium Chloride and 0.27 g of Sulphuric Acid to bring the pH of the aqueous solution in the range of 5.00+//−0.2. Then, by means of syringe, a quantity of Cupreous Chloride (dissolved in water) is added, so as to have a final concentration in the emulsion equal to 4 ppm of Cupreous ion. The solution is stirred to obtain phase homogeneity.

Preparation of the raw emulsion: one acts under the same conditions described in the previous example.

The polymerization reaction: one acts under the same conditions described in the previous example.

The burn-out: Without interrupting either stirring or Nitrogen sparge, 2.00 g of a 1% solution of tert-Butyl hydroperoxide are then additioned and after 5 minutes 10.00 g of a 30% solution of Sodium metabisulfite; the reaction is then kept at the temperature of 45° C., even by heating, for further 60 minutes.

The inversion surfactants: Once the 60 minutes of the previous item have passed, the emulsion is cooled at 25° C. and additivated with 45.90 g of an Alkyl-poly-glycol ether with a HLB 10-12 and 8.10 g of Sodium dioctyl sulphosuccinate. The polymerized and stabilized emulsion is left under stirring for 60 minutes and at last discharged by the reactor.

(Comparative) Example 13: Synthesis of a Poly-Cationic Polymer (AF 100 M SCA) Based Upon Methacryloxyethyltrimethyl Ammonium Chloride (METAC) with the "A" Synthesis Method but by Using a Reaction Temperature for the Acrylamide-Based Products Preparation of the oil phase: 461.82 g of paraffinic, desulphurized and de-aromatized solvent are mixed with 20.5 g of Mono-oleate Sorbitan and 20.5 g of Oleil-isopranolamine. The mixture is let under stirring until phase homogeneity.

Preparation of the aqueous phase: 1162.00 g of Methacryloxy-ethyltrimethyl Ammonium chloride in 80% aqueous solution are mixed with 353.15 g of water by osmosis, 8.83 g of a 1% solution of Potassium bromate, 2.50 g of Isopropyl alcohol, 0.70 g of Diethylenetriaminepentaacetic acid sodium salt, 10.00 g of Ammonium Chloride and 0.27 g di Sulphuric Acid to bring the pH of the aqueous solution if the range of 5.00+/−0.2. Then, by means of syringe, a quantity of Cupreous Chloride (dissolved in water) is added, so as to have a final concentration in emulsion equal to 4 ppm of Cupreous ion.

The solution is stirred to obtain phase homogeneity.

Preparation of the raw emulsion: one acts under the same condition of the previous example.

Polymerization reaction: one acts under the same condition of the previous example.

The burn-out: Without interrupting either stirring or Nitrogen sparge, 2.00 g of a 1% solution of tert-Butyl hydroperoxide are then additioned and after 5 minutes 10.00 g of a 30% solution of Sodium metabisulfite; the reaction is then kept at the temperature of 37.5° C., even by heating, for further 60 minutes.

The inversion surfactants: Once the 60 minutes of the previous item have passed, the emulsion is cooled at 25° C. and additivated with 45.90 g of an Alkyl-poly-glycol ether with a HLB 10-12 and 8.10 g of Sodium dioctyl sulphosuccinate. The polymerized and stabilized emulsion is left under stirring for 60 minutes and at last discharged by the reactor.

The analysis results are shown in table 10 for the anionic ones and table 11 for the cationic ones.

TABLE 10

|  | AF 100 A SCA | Qualifloc AE 3030 | AF 100 AM SCA | Qualifloc AE 3030 M |
|---|---|---|---|---|
| Appearance | E.O. | E.O. | E.O. | E.O. |
| Bulk Viscosity (cPs @ 25° C.) | 1350 | 1350 | 1480 | 1380 |
| (1) UL Viscosity (cPs @ 25° C.) | 24.55 | 49.8 | 20.15 | 47.55 |
| Solids % (w/w) | 38.1 | 38.49 | 42.1 | 39.15 |
| (1) 0.5% solution viscosity (cPs @ 25° C.) | 1850 | 4120 | 2100 | 3900 |
| Dissolution Test (s) | 3 | 3 | 5 | 2 |
| Free monomer (ppm) | <50 | <250 | <50 | <250 |
| Gels % (w/w) | <0.2 | 0.5 | <0.2 | 0.7 |

Legend:
O.E. = Opaque emulsion;
(1) based on dry polymer

TABLE 11

|  | AF 100 SCA | Qualifloc CE 2040 | AF 100 M SCA | Qualifloc CE 2040 M |
|---|---|---|---|---|
| Appearance | E.O. | E.O. | E.O. | E.O. |
| Bulk Viscosity (cPs @ 25° C.) | 1280 | 1280 | 1550 | 1440 |
| (1) UL Viscosity (cPs @ 25° C.) | 5.21 | 23.12 | 4.99 | 22.4 |
| Solids % (w/w) | 47.33 | 42.93 | 43.15 | 44.1 |
| (1) 0.5% solution viscosity (cPs @ 25° C.) | 350 | 2750 | 420 | 2350 |
| Dissolution Test (s) | 12 | 4 | 10 | 5 |
| Free monomer (ppm) | <150 | <250 | <250 | <250 |
| Gels % (w/w) | 0.5 | 0.4 | 0.2 | 0.6 |

Legend:
O.E. = Opaque emulsion;
(1) based on dry polymer

From the results shown in tables 10 and 11 it derives that the "Acrylamide Free" polymer of the SCA series: AF 100 A SCA; AF 100 AM SCA; AF 100 SCA; AF 100 M SCA, have lower values of UL Viscosity and Viscosity in 0.5% solution, with respect to the poly-acrylamide polymers: Qualifloc AE 3030; Qualifloc AE 3030 M; Qualifloc CE 2040; Qualifloc CE 2040 M. This reflects in less molecular weights.

These data demonstrate that the simple replacement of the Acrylamide monomer by different (acrylamide free) monomers, even if structurally correlated to acrylamide, in the classic polymerization process (high temperature) produces polymers having lower chemical/physical features than those which could be obtained with the acrylic monomer (and the classic process) and those which could be obtained with the new synthesis processes developed by the authors.

The invention claimed is:

1. A process for the preparation of an acrylamide-free acrylic polymer comprising:
   preparing a reaction mixture containing a monomer or a mixture of monomers, and polymerization additives,
   adding a polymerization catalyst to the reaction mixture in a controlled manner, and
   allowing a polymerization reaction to proceed until the acrylamide-free acrylic polymer is obtained,
   wherein the monomer and the mixture of monomers do not comprise acrylamide, the reaction mixture is a highly homogenized water-in-oil emulsion with emulsion micelles with sizes in the range of 0.5-1.5 microns, and the polymerization reaction is carried out at a controlled temperature between 30° C. and 45° C. by adding the polymerization catalyst in a controlled manner and by heating or cooling down the mixture.

2. The process according to claim 1, wherein the polymerization catalyst addition takes place by continuously supplying or by pulsed dosing throughout the entire polymerization reaction.

3. The process according to claim 1, wherein water-in-oil emulsion is obtained by mixing an oil phase containing a surfactant having HLB between 3 and 6, and an aqueous phase containing the monomer or the mixture of monomers, the polymerization catalyst and the polymerization additives.

4. The process according to claim 3 wherein the surfactant comprises oleyl-isopropanolamine.

5. The process according to claim 1 wherein the reaction mixture contains the mixture of monomers and the mixture of monomers comprises crosslinking monomers.

6. The process according to claim 1, wherein the reaction mixture includes a monomer composition selected from the group consisting of Acryloxyethyltrimethyl Ammonium chloride (AETAC), Methacryloxyethyltrimethyl Ammonium Chloride (METAC), Dimethylaminoethyl Methacrylate DMS Quaternary, Dimethylaminoethyl Acrylate DMS Quaternary, Dimethyldiallyl Ammonim Chloride (DADMAC), Acrylic Acid, Methacrylic Acid, 2-Acrylamido-2-Methylpropanesulfonic Acid, Sodium Styrenesulfonate and mixtures thereof.

7. The process according to claim 6 wherein the reaction mixture further comprises at least one crosslinking monomer comprising methylene bis-acrylamide or ethylene bis-acrylamide.

8. The process according to claim 1, further comprising adding a large excess of said polymerization catalyst, or a further catalyst, after said adding a polymerization catalyst.

9. The process according to claim 1, further comprising adding an emulsion inversion surfactant having a HLB value between 8 and 18 to the water-in-oil emulsion.

10. An acrylic polymer formed by the process according to claim 1, wherein the acrylic polymer exhibits one or more of:
   a molecular weight between 5 MD and 30 MD;
   a bulk viscosity between 500 cPs and 2500 cPs;
   a UL viscosity between 3 cPs and 60 cPs;
   a percentage of solid between 35% and 50%;
   a viscosity in 0.5% solution at 25° C. between 150 cPs and 4000 cPs; and
   a dissolution time in seconds between 5 s and 15 s.

11. The acrylic polymer according to claim 10, wherein the acrylic polymer includes a monomer composition selected from the group consisting of:
   Acryloxyethyltrimethyl Ammonium chloride (AETAC), Methacryloxyethyltrimethyl Ammonium Chloride (METAC), Dimethylaminoethyl Methacrylate DMS Quaternary, Dimethylaminoethyl Acrylate DMS Quaternary, Dimethyldiallyl Ammonim Chloride (DADMAC), Acrylic Acid, Methacrylic Acid, 2-Acrylamido-2-Methylpropanesulfonic Acid, Sodium Styrenesulfonate and mixtures thereof.

12. A polymeric composition comprising a water-in-oil emulsion comprising an acrylic polymer, the acrylic polymer not containing acrylamide monomer units and exhibiting one or more of:
   a molecular weight between 5 MD and 30 MD;
   a bulk viscosity between 500 cPs and 2500 cPs;
   a UL viscosity between 3 cPs and 60 cPs;
   a percentage of solid between 35% and 50%;
   a viscosity in 0.5% solution at 25° C. between 150 cPs and 4000 cPs; and
   a dissolution time in seconds between 5 s and 15 s,
   and an inversion surfactant with HLB value between 8-18.

13. The acrylic polymer according to claim 10, further comprising methylene bis-acrylamide or ethylene bis-acrylamide.

14. A treatment method comprising:
   mixing the acrylic polymer of claim 10 with a further component by stirring.

15. The treatment method of claim 14, wherein the further component comprises wastewaters or sludge from chemical, physical and/or biological wastewater treatments, and wherein said mixing cleans said wastewaters or sludge from chemical, physical and/or biological wastewater treatments.

16. The treatment method of claim 14, wherein the further component comprises mixtures for paper mills for the production of paper and/or paperboard, and wherein the mixing comprises coagulating said mixtures.

17. The treatment method of claim 14, wherein the further component comprises products of the petrochemical or extraction industry, and wherein the mixing comprises demulsifying or thickening the products.

18. A method for treatment, comprising
   providing the water-in-oil emulsion of claim 12, and
   reversing the water-in-oil emulsion into an oil-in-water emulsion by mixing the water-in-oil emulsion with an aqueous medium.

* * * * *